(12) United States Patent
Baker et al.

(10) Patent No.: US 6,562,850 B1
(45) Date of Patent: May 13, 2003

(54) METHODS OF SYNTHESIZING SULTAMS AND ANTI-VIRAL COMPOSITIONS

(75) Inventors: David C. Baker, Knoxville, TN (US); Anand Mayasundari, Knoxville, TN (US); Jianmin Mao, Knoxville, TN (US); Stephen C. Johnson, Birmingham, AL (US); Shijia Yan, Birmingham, AL (US)

(73) Assignee: The University of Tennessee Research Corporation, TN (US)

( * ) Notice: Subject to any disclaimer, the term of this patent is extended or adjusted under 35 U.S.C. 154(b) by 0 days.

(21) Appl. No.: 09/353,900

(22) Filed: Jul. 15, 1999

Related U.S. Application Data

(63) Continuation-in-part of application No. 09/314,339, filed on May 19, 1999, now Pat. No. 6,353,112.
(60) Provisional application No. 60/093,167, filed on Jul. 17, 1998, and provisional application No. 60/097,225, filed on Aug. 20, 1998.

(51) Int. Cl.$^7$ ..................... C07D 275/06; A61K 31/425
(52) U.S. Cl. ........................................ 514/373; 548/200
(58) Field of Search ........................... 548/207; 514/373

(56) References Cited

U.S. PATENT DOCUMENTS 5,114,949 A * 5/1992 Gueremy .................... 514/293

FOREIGN PATENT DOCUMENTS

| DE | 2105580 | 2/1971 |
| WO | WO 98/42643 | 1/1998 |
| WO | WO 00/18708 | 4/2000 |

OTHER PUBLICATIONS

C.A.123:256581 Doepp, RN 136701–86–5, 1995.*
Hamao Watanabe et al.: "ortho Metalation of N–Substituted Benzenesulfonamides by Excess n–Butyllithium. Condensation with Carbonyl Compounds. Cyclisations", Journal or Organic Chemistry, vol. 33, No. 2, Feb. 1968, pp. 900–903, XP002120991, America Chemical Society, Easton, US ISSN: 0022–3263.

John B. Wright: "The preparation of 2H–1, 2, 3–benzothiadiazine–1, 1–dioxides, 11H–11, 11a–dihydrobenzimidazo [1, 2–b] [1,2 ] benzisothiazole–5, 5–dioxides, 6H–diben zo [c, g] [1, 2, 5]thiadiazocine–5, 5–dioxides and 5H–dibenzo [c, g] [s1, 2, 6]thiadizocine–6, 6–dioxides.", Journal of Heterocyclic Chemistry, vol. 5, No. 4, Aug. 1968, pp. 453–459, XP002120992, Heterocorporation, Provo., US ISSN: 0022–152X, see p. 454, compounds Ia, Ib. IX, X, XI, pp. 457–458.

Mashima, et al. Asymmetric Transfer Hydrogenation of Ketonic Substrates Catalyzed by (n5–C5Me5)MCI Complexes {M–Rh and Ir} of (1S,2S)–N–(p–Toluenesulfonyl)–1,2–diphenylethylenediamine. Chemistry Letters. Dec. 1998, No. 12, pp. 1199–1200.

Mashima, et al. The Half–sandwich Hydride and 16–Electron Complexes of Rhodium and Iridium Containing (1S, 2S)–N–(p–Toluenesulfonyl)–1,2–diphenylethylenediamine: Relevant to Asymmetric Transfer Hydrogenation. Chemistry Letters. Dec. 1998, No. 12, pp. 1201–1202.

Buchwald, Stephen L. et al. Recent Progress in the Suzuki Reactions of Aryl Chlorides. The Strem Chemiker, May 20, vol. XVIII, No. 1.

Mao, Jianmin et al. A Chiral Rhodium Complex for Rapid Asymmetric Transfer Hydrogenation of Imines with High Enantioselectivity. Organic Letters, May 24, 1999, vol. 1, No. 6, pp. 841–843.

* cited by examiner

*Primary Examiner*—Robert Gerstl
(74) *Attorney, Agent, or Firm*—Piper Rudnick LLP

(57) ABSTRACT

The invention relates to a new class of compounds herein identified generally as "sultams", which may be represented by the following formula V, in FIG. 1, in which numbering of the atoms is started with the sulfur atom of the isothiazole. Two of the rings (rings A and C) are aromatic, and the third is a heterocyclic ring (ring B), a cyclic sulfonamide. Of particular importance are the enantiomerically pure sultams since they are especially potent HIV-1 inhibitors.

8 Claims, 6 Drawing Sheets

METHODS OF SYNTHESIZING SULTAMS AND ANTI-VIRAL COMPOSITIONS

CROSS-REFERENCE TO RELATED PATENT APPLICATIONS

This application is based on two earlier provisional patent applications filed under 37 C.F.R. 1.53(b)(2), application Ser. No. 60/093,167 filed on Jul. 17, 1998 entitled Solution Synthesis on Modification of 2,3-Dihydrobenzo[d] isothiazoles, and application Ser. No. 60/097,225 filed on Aug. 20, 1998 entitled A Solid-Phase Synthesis and Combinatorial Approach to 2,3-Dihydrobenzo[d]isothiazoles 1,1-dioxides that are Substituted at the 2- and/or 3-Positions. This application is a continuation-in-part of application Ser. No. 09/314,339 filed on May 19, 1999 U.S. Pat. No. 6,353,112. This application claims the benefit of the filing dates of all three above-identified applications, which are incorporated herein by reference in their entirety.

STATEMENT REGARDING FEDERALLY SUPPORTED RESEARCH

This invention was made with government support under Contract/Grant N01-CM-67261 awarded by the National Cancer Institute. The government has certain rights in this invention.

BACKGROUND OF THE INVENTION

In 1982 physicians first became aware of a new sexually transmitted disease that was associated with an unusual form of cancer (Kaposi's sarcoma) and a variety of unusual infections. The disease was named acquired immune deficiency syndrome (AIDS), since both these problems reflected a severe deficiency in the helper T cells of the immune system. A retrovirus, called human immunodeficiency virus (HIV), was found to be the causative agent of AIDS. HIV is a member of a family of viruses called lentiviruses that are part of a large group of viruses known as the Retroviridae. Some of the other members of the group are the closely related simian, feline, and bovine immunodeficiency viruses. This group of viruses displays a variety of common features.

The fact that HIV has an extreme tendency to mutate to forms that are resistant to existing antiviral therapies greatly complicates attempts to treat the infection with antiviral drugs. Most of the current research in AIDS is aimed at understanding the life cycle of HIV. AIDS research has been targeted towards inhibition of the virus at different stages of its life cycle.

The molecular target for HIV inhibitors can be broadly classified into the following classes: reverse transcriptase (RT) enzyme, protease enzyme, integrase enzyme, regulatory proteins, and zinc finger domains in the nucleocapsid p7 protein.

The normal flow of genetic information is from DNA to RNA to protein, and hence HIV, which is a retrovirus, must first convert its genomic RNA into a double-stranded DNA in order to start its replication cycle in the host cell. This conversion takes place in the host cell cytoplasm with the help of a viral enzyme called reverse transcriptase (RT) that catalyzes a series of biochemical reactions involved in this process. This makes reverse transcriptase (RT) enzyme an attractive target for HIV inhibitors. HIV RT inhibitors can be broadly classified into nucleoside (NRTIs) and non-nucleoside RT inhibitors (NNRTIs). The modes of action of these two classes of compounds are different in nature. The nucleoside HIV RT inhibitors are competitive inhibitors that bind to the catalytic site of the enzyme, and their mode of action appears to be through their triphosphates (produced in the cytoplasm of the host cell) that act as RT enzyme inhibitors through incorporation and termination of the growing viral DNA chain. Common nucleoside RT inhibitors are AZT, ddC, ddI, d4T, 3TC, and Abacavir. Non-nucleoside RT inhibitors are non-competitive inhibitors of the RT enzyme; they bind to an allosteric (regulatory) site with a degree of magnitude heretofore not yet observed and influence the RT catalytic site. Hence they are also referred to as second-site inhibitors. In general, at micromolar concentrations NNRTIs inhibit HIV-1 in vitro with minimum or no cytotoxicity but do not inhibit HIV-2 or other retroviruses. NNRTIs include chloro-TIBO, nevirapine, L-697, 661, and delavirdine.

1. Field of the Invention

The need and research for active inhibitors of human immunodeficiency virus-1 reverse transcriptase (HIV-1 RT) is urgent and ongoing. In 1997, U.S. Pat. No. 5,608,085 issued to Baker et al. entitled Synthesis of Optically Active Calanolides A and B and Enantiomers and Related Compounds, which produces anti-HIV-1 or HIV-2 compounds in high yields and in a high degree of purity. Recently, on Dec. 1, 1998, U.S. Pat. No. 5,843,990 issued to Baker et al. entitled Pyran-Chromenone Compounds, Their Synthesis and Anti-HIV Activity, which deals with a class of compounds, particularly optically active compounds of a high degree of purity and free of the corresponding enantiomers, which are highly potent anti-HIV compounds. Application by Deshpande et al. (Ref. 22) also claims this contribution to the scientific community. The effectiveness of these compounds as HIV-1 inhibitors depends on many factors including the degree of affinity these HIV-1 inhibitors have for the enzyme's allosteric site. In accordance with this invention, novel 2,3-dihydrobenzo[d]isothiazole 1,1-dioxides (sultams) have been discovered that are biologically active, particularly potent HIV-reverse-transcriptase inhibitors. Further, a novel synthesis has been discovered (and a number of variants) by which the sultams are synthesized in an efficient, multi-step process from which the pure enantiomers of the racemates are obtained.

2. Description of Related Art

Publications of interest relating to the subject matter of this invention include:

1. Wilson, S. R., & Czarnik, A. W. (1997) *Combinatorial Chemistry*, John Wiley & Sons, Inc., New York.
2. Gulakowski et al. (1991) *J. Virol. Meth.*, 33:87–100.
3. Hermkens, P. H. H., Ottenheijm, H. C. J., & Reeds, D. (1996) *Tetrahedron* 52:4527–4554.
4. Hermkens, P. H. H., Ottenheijm, H. C. J., & Reeds, D. (1997) *Tetrahedron* 53:5643–5678.
5. Watanabe, H., Gay, R. L., & Hauser, C. R. (1968) *J. Org. Chem.* 33:900–903.
6. Plunkett, M., Ellman, J. A. (1997) *J. Org. Chem.* 62:2885–2893.
7. Woolard, F. X., Paetsch, J., & Ellman, J. A. (1997) *J. Org. Chem.* 62:6102–6103.
8. Beaver, K. A., Siegmund, A. C., & Spear, K. L. (1996) *Tetrahedron* 37:1145–1148.
9. Halm, C., Evarts, J., & Kurth, M. J. (1997) *Tetrahedron Lett.* 38:7709–7712.
10. Seeberger, P. H., Beebe, X., Sukenick, G. D., Pochapsky, S., & Danishefsky, S. J. (1997) *Angew. Chem., Int. Ed. Engl.*, 36:491–493.
11. Kim, S. W., Hong, C. Y., Lee, K., Lee, E. J., & Koh, J. S. (1998) *Bioorg. Med. Chem. Lett.* 8:735–738.

12. Beaver, K. A., et al. (1989) U.S. Pat. No. 4,859,736.
13. Nicolaou, K. C., Xiao, X.-Y., Pasandoosh, Z., Senyei, A., & Nova, M. P. (1995) *Angew. Chem., Int. Ed. Engl.* 34:2289–2291.
14. Moran, E. J., Sarshar, S., Cargill, J. F., Shahbaz, M. M., Lio, A., Mjalli, A. M. M., & Armstrong, R. W. (1995) *J. Am. Chem. Soc.* 117:10787–10788.
15. European Patent Application No. O 422 944 A1, published on Apr. 17, 1991, entitled *Chiral Sultams*.
16. Snieckus, V. (1996) *Chemical Synthesis: Gnosis to Prognosis*, Chatagilialoglu, C. & Snieckus, V. (eds.) Kluwer Academic Publishers, Dordrecht, 191–221.
17. Alerton, E., et al. (1981) *Proc. Am. Pept. Symp.*, Pierce Chemical Company, Rockford, Ill., 163–195.
18. Weislow, O. W., et al. (1989) *J. Natl. Cancer Inst.* 81:577–586.
19. Eliel, E. L. & Wilen, S. H. (1994) *Stereochemistry of Organic Compounds*, John Wiley & Sons Inc., New York, 24.
20. Remington's Pharmaceutical Sciences, Mack Publishing Co., Easton, Pa., USA.
21. Corbett, J. W. (1998) *Org. Prep. Proc. Int.* 30:489–550.
22. Deshpande, P. P., Tagliaferri, F., Victory, S. F., Yan, S., & Baker, D. C. (1995) *J. Org. Chem.* 60:2964–2965.
23. Watanabe, H., et al. (1968) *J. Org. Chem.* 33:900–903.
24. DeClercq, E. (1993) *Med. Res. Rev.* 13:229.
25. Kilby, M. J., Saag, M. S. (1996) *Antiviral Chemotherapy 4: New Directions for Clinical Application and Research*, Mills, J., Volberding, P. A., & Corey, L. (eds) Plenum Press, New York, 291–298.
26. Romero, D. L., Morge, R. A., Genin, M. J., Biles, C., Busso, M., Resnick, L., Altaus, I. W., Reusser, F., Thomas, R. C., Tarpley, W. G. (1993) *J. Med. Chem.* 36:1505.
27. Dueweke, T. J., Poppe, S. M., Romero, D. L., Swaney, S. M., So, A. G., Downey, K. M., Althaus, I. W., Reusser, F., Busso, M., Resnick, L., Mayers, D. L., Lane, J., Aristoff, P. A., Thomas, R. C., Tarpley, W. G. (1993) *Antimicrob. Agents Chemother.* 37:1127.
28. Vasudevachari, M. B., Battista, C., Lane, H. C., Psallidopoulos, M. C., Zhao, B., Cook, J., Palmer, J. R., Romero, D. L., Tarpley, W. G., Salzman, N. P. (1992) *Virology* 190:269.
29. Merluzzi, V. J., Hargrave, K. D., Labadia, M., Grozinger, K., Skoog, M., Wu, J. C., Shih, C. K., Eckner, K., Hattox, S., Adams, J., Rosehthal, S. A., Frances, R., Eckner, R. J., Koup, R. A., Sullivan, J. L. (1990) *Science* 250:1411.
30. Lehninger, A. L., Nelson, D. L., Cox, M. M. (1993) *Principles of Biochemistry*, 2nd ed., Worth Publishers, New York.
31. Carey, F. A. & Sundberg, R. S. (1977) *Advanced Organic Chemistry*, 3rd ed., Plenum Press, New York, 677–699.

All references referred to in this text are incorporated herein by reference in their entirety.

SUMMARY OF THE INVENTION

The invention relates to a new class of compounds herein identified generally as "sultams", which may be represented by the following formula V, in FIG. 1, in which numbering of the atoms is started with the sulfur atom of the isothiazole. Two of the rings (rings A and C) are aromatic, and the third is a heterocyclic ring (ring B), a cyclic sulfonamide. Of particular importance are the enantiomerically pure sultams since they are especially potent HIV-1 inhibitors.

Sultams are derivatives of isothiazole 1,1-dioxide (cyclic 5-membered sulfonamides) with an aromatic ring fused at the C-4 and C-5 positions of the isothiazole ring. The investigated sultams have various substituents on the aromatic rings. The nitrogen of the sulfonamide is either tertiary or secondary depending on the nature of the substituents on that atom. On the C-3 position of sultams a variety of aromatic substituents is possible depending on whether aldehydes or ketones are used in the synthesis of the ortho-alkylated sulfonamide IV from FIG. 1. The other substituents on the same carbon can either be hydrogen, when an aldehyde is the reactant, or another substituent defined further below. This quaternary carbon determines the chirality of the resulting sultam. A racemic substance comprised of a pair of enantiomers is generally the product of synthesis and preferably should be separated into the respective enantiomers.

The invention promotes a general method and several synthesis variations more suitable for certain compounds, as described hereinafter. Synthesis variations are taught by the invention that provide a variety of substituents on the rings of the compounds. One such synthesis is better suited for starting compounds with halogen substituents on ring A, which are not compatible with the reaction conditions used in the general method. Another synthesis variation is better suited for compounds which have substituents on ring C which are susceptible to react in subsequent steps of the reaction. These compounds are provided with a protective group for the substituents, which is subsequently removed. Another synthesis variation of the invention yields compounds wherein $R^Q$ is $CF_3$. Another synthesis variation of the invention yields compounds in which all the substituent R groups are hydrogens. These syntheses are described in further detail hereinafter. The syntheses of the invention are highly versatile in that the variant best suited for the class of compounds of interest is the synthesis by which one can obtain either a racemic mixture of the pairs of enantiomers or the pure enantiomer, which is the most potent for the control of the target virus.

An objective of the synthesis was to obtain biologically active compounds, especially anti-HIV-1 compounds. The sultam compounds of the invention offer a variety of structural modifications and various possibilities of positioning different substituents in different positions on any one of the rings. It was not known prior to this invention what effect these various substituents and their different positions on the nitrogen, on the stereogenic carbon, and on the ring(s) would have on their biological and, more particularly, their anti-HIV-1 activity.

The invention also provides a new class of such compounds in racemic form which can be resolved into their respective enantiomers. A group of these compounds has an anti-HIV potency heretofore unachieved. In accordance with the invention, an area of the molecule has been identified on which appropriate substituents appear to make a major contribution to a high degree of anti-HIV potency.

The invention also provides a method for treating or preventing viral infections, especially strains of the HIV virus, with the sultams of the invention.

The invention also provides biologically active compositions, which comprise one or more compounds of the invention, in an effective, non-toxic amount in combination with a biologically or pharmaceutically acceptable carrier.

The invention also provides drug combinations of compounds of the invention with HIV protease inhibitors, like ritonavir, saquinavir mesylate, and others.

In still another aspect, the invention provides a method for treating a mammal, particularly a human, infected with a retrovirus, which comprises administering to said mammal an effective nontoxic amount of the composition(s) of the invention.

In summary, the invention contributes to the solution for a serious and urgent world-wide health need which has adverse social and economic consequences.

DETAILED DESCRIPTION OF THE INVENTION

The Compounds of the Invention

Figure 1:
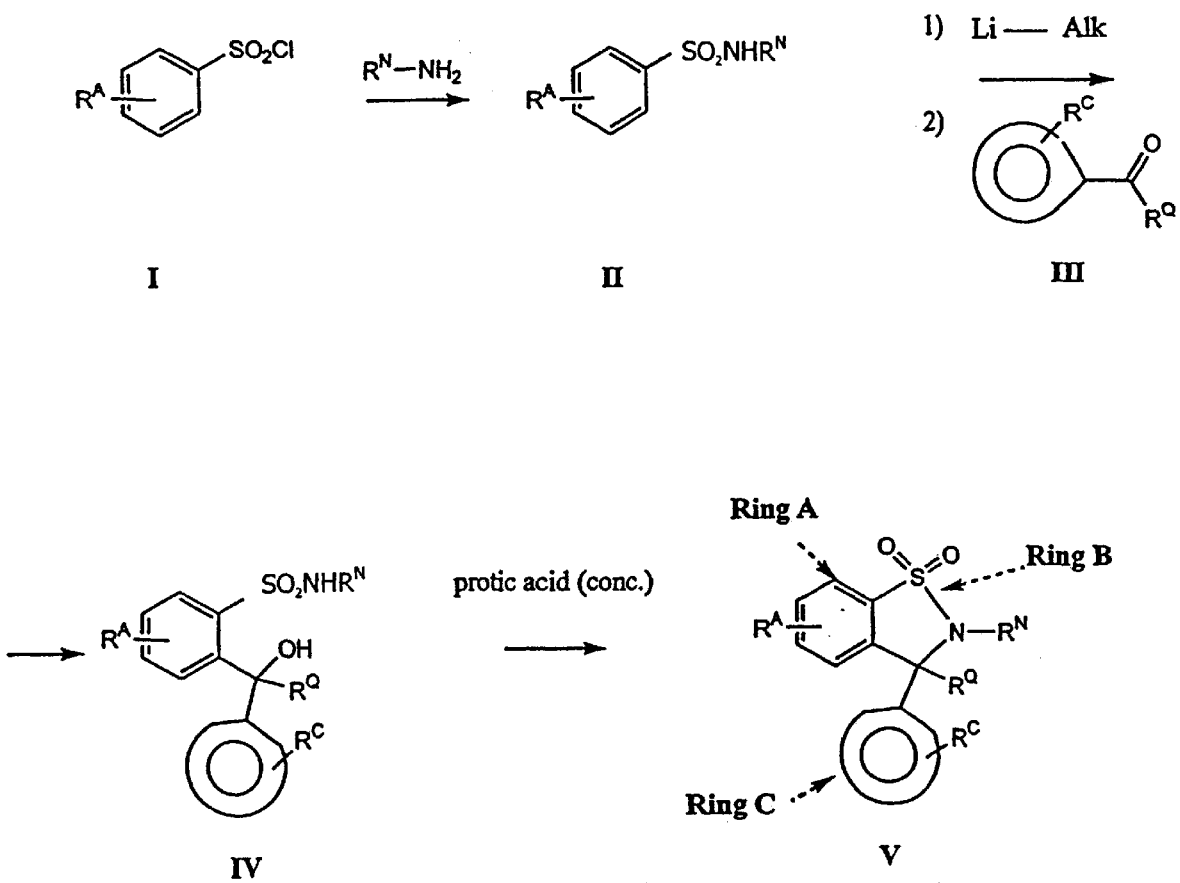
FIG. 1 shows a general scheme of the synthesis of sultams.

The sultams of the invention include the compounds of formula V, as shown in FIG. 1, in which $R^A$ is hydrogen, a linear- or a branched-chain hydrocarbon (saturated or unsaturated) such as alkyl, preferably lower alkyl, and a halogen such as chlorine, bromine, iodine, or fluorine.

$R^N$ is hydrogen, a linear- or branched-hydrocarbon (saturated or unsaturated) such as alkyl, preferably lower alkyl or aryl.

$R^Q$ is hydrogen, a linear- or branched-hydrocarbon (saturated or unsaturated) such as alkyl, preferably lower alkyl, a substituted alkyl such as $CF_3$, aryl, alkyl-substituted aryl, a heterocyclic, such as pyridinyl, picolinyl, where the heteroatoms can be nitrogen, oxygen, or sulfur, and fused rings such as naphthyl, or quinolinyl.

$R^C$ is hydrogen, a linear- or branched-hydrocarbon (saturated or unsaturated), such as alkyl, preferably lower alkyl, a halogen such as chlorine, bromine, iodine, or fluorine, hydroxyl, alkoxyl, preferably lower alkoxyl, or an amide such as an acylamide.

Other than a benzene ring, ring A can also be a heterocyclic ring such as furyl or a polycyclic ring, provided that it generates only one species upon ortho-lithiation with alkyllithium, as opposed to isomers. For example, pyridine-4-sulfonyl chloride (Compound I, in FIG. 1) can be ortho-lithiated only at the 3-position of pyridine (numbered from the nitrogen). Preferably, the polycyclic ring has carbon atoms, and when it is a heterocyclic ring, the heteroatoms can be nitrogen or sulfur.

Ring C can also be a heterocyclic or polycyclic aromatic ring provided that the corresponding aldehyde or ketone is sufficiently reactive in the reaction. An aliphatic aldehyde can also be used, resulting in a sultam with an aliphatic substituent rather than an aromatic ring C.

The sultam in which all substituents are hydrogen, but for $R^N$, which is methyl, namely (±)-2-methyl-3-phenyl-2,3-dihydrobenzo[d]isothiazole 1,1-dioxide, is a known compound as disclosed by Watanabe et al. The compound is included among the compounds made by the synthesis of the invention because, as far as is known, it had never been made by this method.

TABLE I

| Compound | $R^A$ | $R^N$ | $R^Q$ | $R^C$ |
|---|---|---|---|---|
| 1 | H | Me | H | H |
| 2 | (S)-enantiomer of 1. | | | |
| 3 | (R)-enantiomer of 1. | | | |
| 4 | H | Me | H | 3-Me |
| 5 | (S)-enantiomer of 4. | | | |
| 6 | H | Me | H | 3-F |
| 7 | (S)-enantiomer of 6. | | | |
| 8 | H | Me | H | 3-Cl |
| 9 | (S)-enantiomer of 8. | | | |
| 10 | (R)-enantiomer of 8. | | | |
| 11 | H | Me | H | 3-Br |
| 12 | (S)-enantiomer of 11. | | | |
| 12a | H | Me | H | 2-I |
| 13 | H | Me | H | 3-I |
| 14 | H | Me | H | 3-$CF_3$ |
| 15 | H | Me | H | 3-OH |
| 16 | H | Me | H | 2-Cl |
| 17 | H | Me | H | 2-Me |
| 18 | H | Me | H | 4-Me |
| 19 | (R)-enantiomer of 18. | | | |
| 20 | H | Me | H | 4-OH |
| 21 | (S)-enantiomer of 20. | | | |
| 21a | H | Me | H | 2-Br |
| 22 | (R)-enantiomer of 20. | | | |
| 22a | H | Me | H | 2-F |
| 23 | H | Me | H | 4-OMe |
| 24 | (R)-enantiomer of 23. | | | |
| 25 | H | Me | H | 4-$NH_2$ |
| 26 | H | Me | H | $NHCOCH_3$ |
| 27 | H | Me | H | 4-F |
| 28 | H | Me | H | 4-Cl |
| 29 | H | Me | H | 4-Br |
| 30 | H | Me | H | 4-Ph |
| 31 | H | Me | H | 2-Me, 5-Me |
| 32 | H | Me | H | 2-Cl, 3-Cl |
| 33 | H | Me | H | 2-Cl, 6-Cl |
| 34 | H | Me | H | Ring C = $C_6F_5$ |
| 35 | H | H | H | H |
| 36 | H | H | H | 3-Cl |
| 37 | H | Et | H | 3-Cl |
| 38 | H | Bu | H | 3-Cl |
| 39 | H | t-Bu | H | 3-Cl |
| 40 | H | Ph | H | H |
| 41 | H | 2-Pr | H | H |
| 42 | H | Me | Me | H |
| 43 | H | Me | Me | 2-Cl |
| 44 | H | Me | Me | 3-Cl |
| 45 | H | Me | Me | 3-OH |
| 46 | H | Me | $CF_3$ | M |
| 47 | 5-Me | Me | H | H |
| 48 | 5-Me | Me | H | 3-Cl |
| 49 | 5-Me | Me | H | 4-F |
| 50 | 5-Me | Me | H | Ring C = 2-furyl |
| 51 | 5-Me | Me | H | 4-OH |
| 52 | 5-Me | Me | H | 4-OMe |
| 53 | 5-Me | Me | Me | H |
| 54 | 5-Cl | Me | H | H |
| 55 | 5-Cl | Et | H | H |
| 56 | 5-Cl | Pr | H | H |
| 57 | H | Me | H | 3-Et |
| 58 | H | Me | H | 3-Vinyl |

METHODS OF THE INVENTION

A general method of the invention comprises: sulfonating a primary amine with an aromatic sulfonyl chloride, thereby obtaining a secondary aryl sulfonamide; lithiating secondary aryl sulfonamide at the ortho-position with a lower alkyllithium in an real solvent, thereby obtaining a lithiated sulfonamide; alkylating said lithiated sulfonamide with an (aromatic) aldehyde or ketone, thereby obtaining the ortho-alkylated sulfonamide; and cyclizing the said ortho-alkylated sulfonamide with a strong organic or inorganic acid, thereby obtaining a racemic mixture of sultam.

In a more detailed description, the method preferably proceeds as follows. To a primary amine, such as methyl amine, in a basic aqueous solution, such as sodium hydroxide in water, there is added an aromatic sulfonyl chloride, such as p-toluenesulfonyl chloride, at low temperature, preferably between about −5° C. and about 5° C. The reaction is stirred for about three hours within the same temperature range. After the mixture is diluted with water, the product, a secondary aryl sulfonamide II, can be extracted with organic solvent such as ethyl acetate from the reaction mixture.

The sulfonamide species is then lithiated at the ortho-position with an excess (ca. 2.5 equivalents) of a lower alkyllithium such as butyllithium, in a dry ethereal solvent such as tetrahydrofuran at low temperature, preferably between about −5° C. and about 5° C. The solvent is preferably freshly distilled from a suitable drying agent, such as sodium or sodium-benzophenone ketyl, to avoid the presence of moisture in this reaction. The alkyllithium solution, such as butyllithium in hexanes, is added to the reaction gradually. After the lithiation is complete (ca. after about 30 minutes at the same temperature range), a solution of an aldehyde or ketone, such as benzaldehyde or methylphenyl ketone in an ethereal solvent such as tetrahydrofuran, is added gradually to the mixture at the same temperature range. The reaction can then be stirred to completion in about 45 min in the same temperature range. The carbanion species at the ortho-position of the sulfonamide attacks the carbonyl carbon on the aldehyde or ketone and forms an hydroxyl group on the benzylic position. In this manner, the alkylated sulfonamide is obtained.

Next, the alkylated sulfonamide is treated with an inorganic or organic strong acid, such as sulfuric acid, hydrochloric acid, hydrobromic acid, or trifluoroacetic acid, at ambient or elevated temperature, such as refluxing temperature, for a time sufficient to complete the reaction, for example, about 1.5 to 6 hours. Alternatively, a suitable Lewis acid, such as aluminum chloride or zinc chloride, may be used. After dilution of the reaction mixture with ice, the product can be separated with an organic solvent such as methylene chloride. The acid protonates the benzylic alcohol to generate a suitable leaving group (water) at the carbon, which is subsequently attacked by the electron pairs on the nitrogen atom and forms cyclized sulfonamide. The final product obtained is a racemic mixture.

The alkyllithium, sometimes hereinafter referred to as "Li-Alk," which is selected for reaction with the aryl sulfonamide, is preferably a lower alkyllithium where alkyl can be linear or branched of 1 to 6 carbons, such as methyl, ethyl, propyl, isopropyl, isobutyl, butyl or the like. Since the selection of the aromatic aldehyde or ketone determines the nature of ring C and its substituents, $R^C$, as well as the $R^Q$ group, a great variety of such reactants are suitable. Ring C can be an aromatic ring such as phenyl or furyl, preferably phenyl.

When an aldehyde is used in the synthesis, ideally $R^C$ is hydrogen; and alkyl or alkenyl group (with two or three double bonds) having 1 to 6 carbon atoms, more preferably 1 to 4 carbon atoms, linear or branched-alkenyl such as ethenyl, propenyl, butenyl, isopropenyl, and the like or alkyl such as methyl, butyl, isobutyl, propyl, isopentyl; a halogen such as chlorine, bromine, or fluorine; a hydroxyl group; an alkoxy group such as methoxy; or an acylamido group such as acetamido. $R^Q$ is preferably hydrogen, generating an aldehyde for greater reactivity. When a ketone is used in the synthesis, $R^Q$ can be an alkyl or alkenyl group as defined above, preferably methyl; a substituted alkyl such as $CCl_3$, $CF_3$ and the like; or one of aryl-alkyl, heteroaryl, aryl, or polycyclic, such as bicyclic. The heteroatom can be nitrogen, oxygen, or sulfur.

A Method of Synthesis of Sultam V (FIG. 1)

The general method of the invention comprises reacting a primary amine with an aromatic sulfonyl chloride I under reactive conditions, preferably in a basic aqueous medium. There is obtained a secondary aryl sulfonamide II which may be isolated. Sulfonamide II is then selectively lithiated at the ortho-position with an organic lithium reactant under reactive conditions. Thereafter, the lithiated sulfonamide is alkylated with an aldehyde or a ketone III under reactive conditions. During the reaction, the carbanion species at the ortho-position of the sulfonamide II attacks the carbonyl carbon on the aldehyde of ketone III forming an hydroxide group on the benzylic ring, thereby obtaining alkylated sulfonamide IV. The synthesis proceeds by treating the alkylated sulfonamide IV with a strong organic or inorganic acid under reactive conditions. The acid provides protons to the benzylic alcohol generating a leaving group at this carbon, which is subsequently attacked by the electron pairs on the nitrogen atom, thus forming the cyclized sulfonamide sultam V. The product is obtained in a racemic mixture.

In the first step of the synthesis, the primary amine reactant may be any primary amine, preferably a lower alkyl amine, wherein the alkyl group is ideally not longer than four carbon atoms. The reaction is more preferably carried out in an aqueous basic medium such as a soluble metal hydroxide in water. Any aromatic sulfonyl chloride may be used, such as p-toluenesulfonyl chloride. The temperature should be low, preferably between about −5° C. and about 5° C. The secondary aryl sulfonamide II is soluble in and extractable with an organic solvent such as a low alkyl acetate, preferably ethyl acetate or other organic solvents.

An ideal reactant for lithiating the sulfonamide II at the ortho-position is a lower alkyllithium such as butyllithium. The reaction should be carried out in a dry ethereal solvent such as tetrahydrofuran at a low temperature, preferably between about −5° C. and about 5° C. Moisture should be avoided in this reaction. Any aldehyde or ketone III, but preferably benzaldehyde or methylphenyl ketone in an ethereal solvent, such as tetrahydrofuran may be added to lithiate the sulfonamide.

The strong acid with which the alkylated sulfonamide IV is treated may be any inorganic strong acid such as sulfuric, hydrobromic or hydrochloric acid or a strong organic acid such as trifluoroacetic acid. The reaction is generally carried out at ambient or preferably at elevated temperature, such as refluxing temperature, and for a time sufficient to complete the reaction, such as approximately 1.5 to 6 hours. The product can be extracted with an organic solvent such as methylene chloride. Final product V is obtained in a racemic mixture which can be separated into the respective enantiomers by methods described hereinafter.

Methods of Synthesizing Sultams VI by Masking Functionally Active Groups with a Protective Group In accordance with the invention, variants of the synthesis have been developed for sultams which have heteroatom substituents on ring C which are prone to react and, thus, disrupt the synthesis. The variants provide protective groups to the substituents, which are subsequently removed. Typical substituents are hydroxyl and amino groups.

Figure 3:
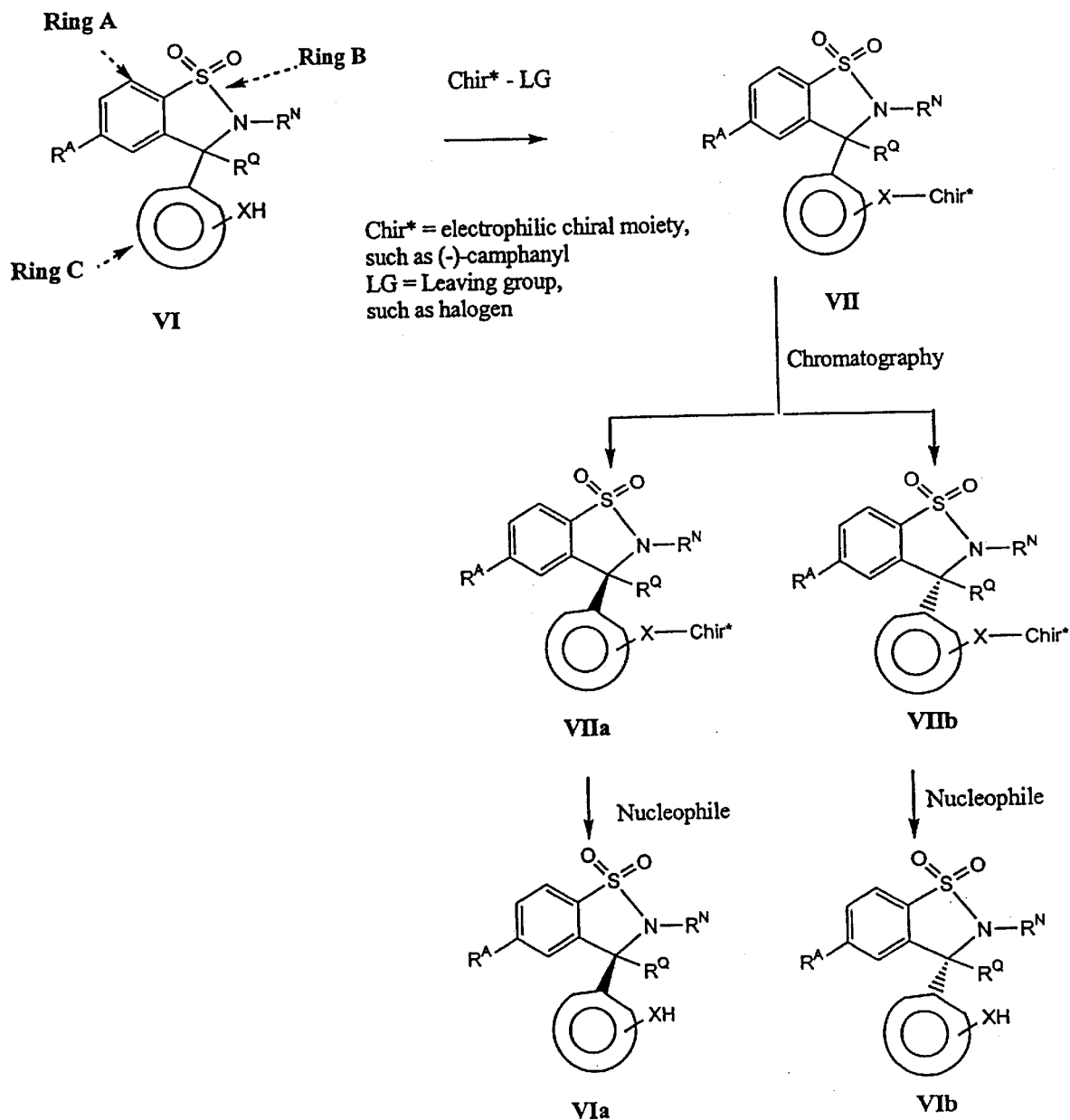
FIG. 3 shows the separation of pairs of enantiomers into their respective pure forms.

One variant of the method of the invention comprises: removing the protective group from the substituent on ring C, thereby obtaining a racemic mixture of sultam VI as shown in FIG. 3, which is R-substituted on ring C; reacting sultam VI with an electrophilic chiral reagent such as (−)-camphanic acid chloride or (R)-(−)-alpha-methoxy-alpha-(trifluoromethyl)phenylacetyl chloride, thereby introducing an additional chiral center in sultam VI, and forming a mixture of a pair of diastereomers VIIa and VIIb; and separating the two diastereomers by running said diastereomeric mixture on a chromatography column with a different affinity for each diastereomer and collecting at least one of the two diastereomers.

In accordance with a variant of the invention, it has been found that the synthesis of sultams VI (FIG. 2) which contain di- or polyvalent heteroatom substituents such as an hydroxyl or amino group on ring C, it is best to modify the functional substituents with protecting groups (PGs) which cause the substituents to be less reactive to avoid interference during the subsequent synthetic steps. Substituents which are prone to react in the subsequent steps of the reaction include an amino group which reacts with the alkyllithium or the hydroxyl group which is deprotonated to give salts in the subsequent steps. Such substituents can be directly or indirectly linked to ring C, that is, by the intermediary of one or more carbon atoms. The method provides for masking the reactive groups with protective groups (PGs) which transform the substituents to less reactive ones to avoid side reactions during the synthesis steps. The protecting groups should be passive under the reaction conditions of the synthesis and readily removable when necessary without affecting other parts of the molecule. A suitable choice of PG for hydroxyl substituents is an alkyl group. Protection of primary or secondary amino substituents may be achieved by masking the nucleophilicity of the amino group through derivatization with, for example, t-butoxycarbonyl (TBOC) or carbobenzyloxy ($CB_2$).

Other suitable protecting groups are known in the art as exemplified by Green, T. W., and Wuts, P. G. M. (1991) *Protective Groups in Organic Synthesis,* 2nd ed., John Wiley & Sons Inc., New York.

When the PG on sultam V is an aryl group such as acetyl, it may be removed with a protic acid, such as diluted hydrochloric acid, at elevated temperature for a necessary time, such as approximately 1 hour. The deprotected sultam VI can be obtained by extraction from the neutralized reaction mixture with a suitable organic solvent, such as methylene chloride. When the PG is an alkyl group such as methyl, it can be removed by a Lewis acid, such as boron tribromide, at low temperature, preferably between −90° C. and −70° C., under an inert atmosphere, such as nitrogen. After warming the reaction mixture to ambient temperature, the reaction is completed generally in about 2 to 5 hours. Product VI can be extracted from the reaction mixture, preferably cooled, with an organic solvent such as methylene chloride.

If desired, ring C substituent compounds can be converted to the corresponding unsubstituted ring compound. For example, an amino group on ring C can be removed by amide hydrolysis followed by deamination.

Method to Synthesize Pure Enantiomers and to Separate Racemates into Enantiomers Several attempts to separate racemic mixtures of the respective enantiomers were not successful. In a first attempt, the hydroxyl or amino ring C of substituted sultam VI, as shown in FIG. 3, was reacted with either an enantiomer of electrophilic chiral reagent (Chir*-LG, such as (−)-camphanic acid chloride or (R)-(−)-alpha-methoxy-(trifluoromethyl)phenylacetyl chloride) to introduce an additional chiral center to sultam VII, thus forming a pair of diastereomeric amides or esters VIIa and VIIb. It was expected that the two diastereomers, VIIa and VIIb could be separated by either achiral or chiral column chromatography due to the different degrees of interaction with the stationary phase of the column. Contrary to expectations, VII could not be separated well into VIIa and VIIb either on a regular silica gel column nor Diacel's Chiralcel OD HPLC column.

Figure 2:
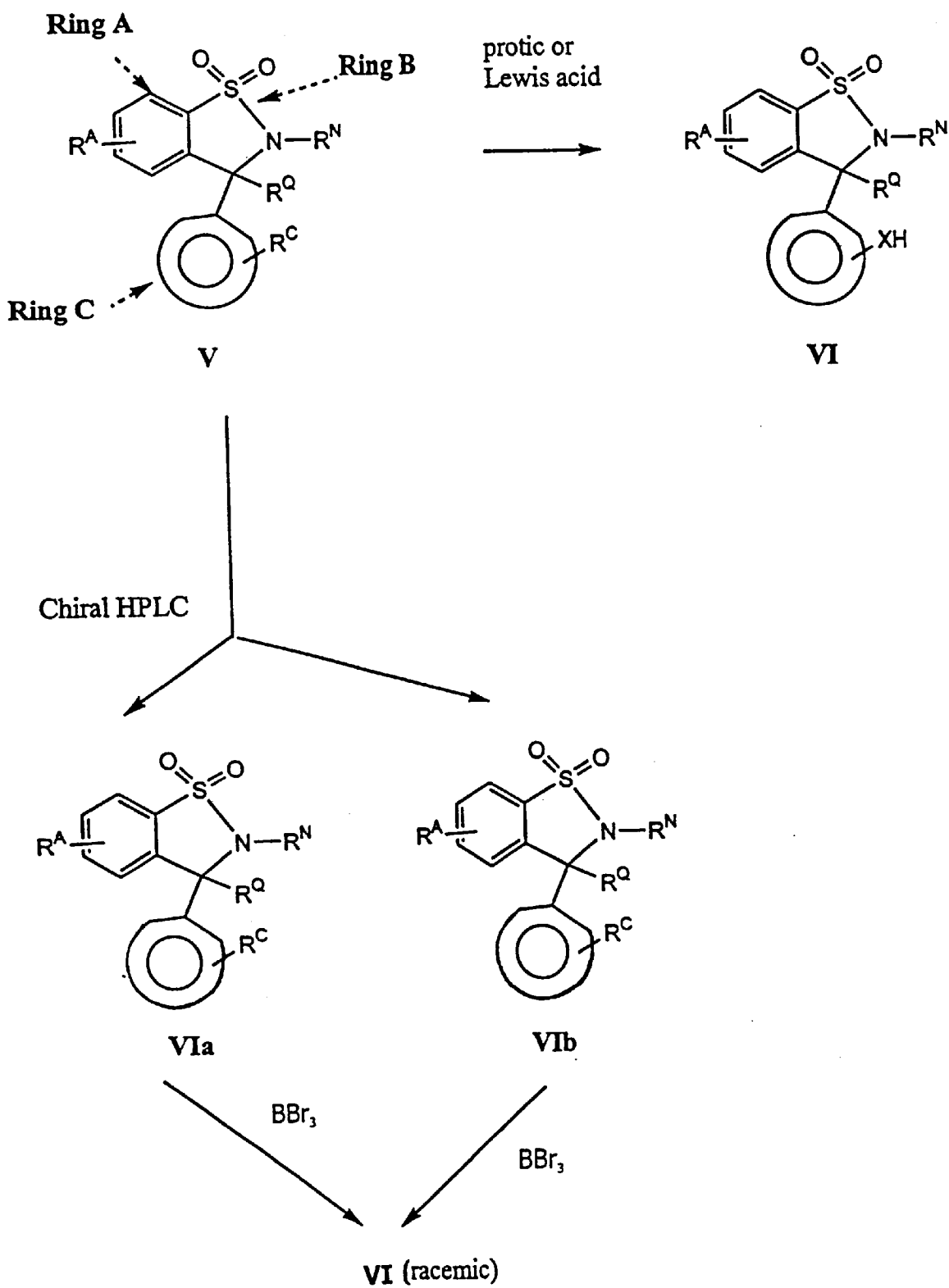
FIG. 2 shows the synthesis from compounds that have functional substituents on ring C modified by a protective group which is subsequently removed.

Another alternative as shown in FIG. 2 was to synthesize p-methoxy substituted ring C analog V as a protected hydroxyl sultam. The pair of racemic compounds VIa and VIb separated on a chiral HPLC column. Nevertheless, when treated with a Lewis acid, such as boron tribromide, to convert the methoxyl to an hydroxyl group, the enantiomerically pure hydroxy compound was racemized back to mixture VI.

Finally, after reacting the racemic hydroxyl sultams with chiral acid chloride, for example, (−)-camphanic acid chloride, in the presence of a catalyst, such as DMAP, the pair of diastereomeric esters VIIa and VIIb as shown in FIG. 3 were separated successfully from each other by Diacel's Chiralcel OD HPLC column. The separated enantiomers were hydrolyzed to the corresponding chiral phenols (or hydroxyl sultams) VIa and VIb under suitable conditions, such as 40% ammonia in methanol. The pure enantiomers were obtained.

Determination of the Absolute Stereochemistry

One of the hydroxyl sultams VIa or VIb as shown in FIG. 3 was crystallized from a suitable solvent system, such as hexanes-ethyl acetate, and its single crystal X-ray structure was obtained. The absolute configuration of the stereogenic center (C-3 carbon of sultam VIa) was determined by the relation to the known chirality of the auxiliary moiety and was assigned as 'S' relative to the known '1S' configuration of the (−) isomer. The compound and the p-hydroxy analog have the same carbon skeleton and a remote hydoxyl group which is not expected to affect the sign of optical rotation of the sultam. Accordingly, it was concluded that the compound has the same absolute configuration, namely, an (S) configuration.

Figure 4:
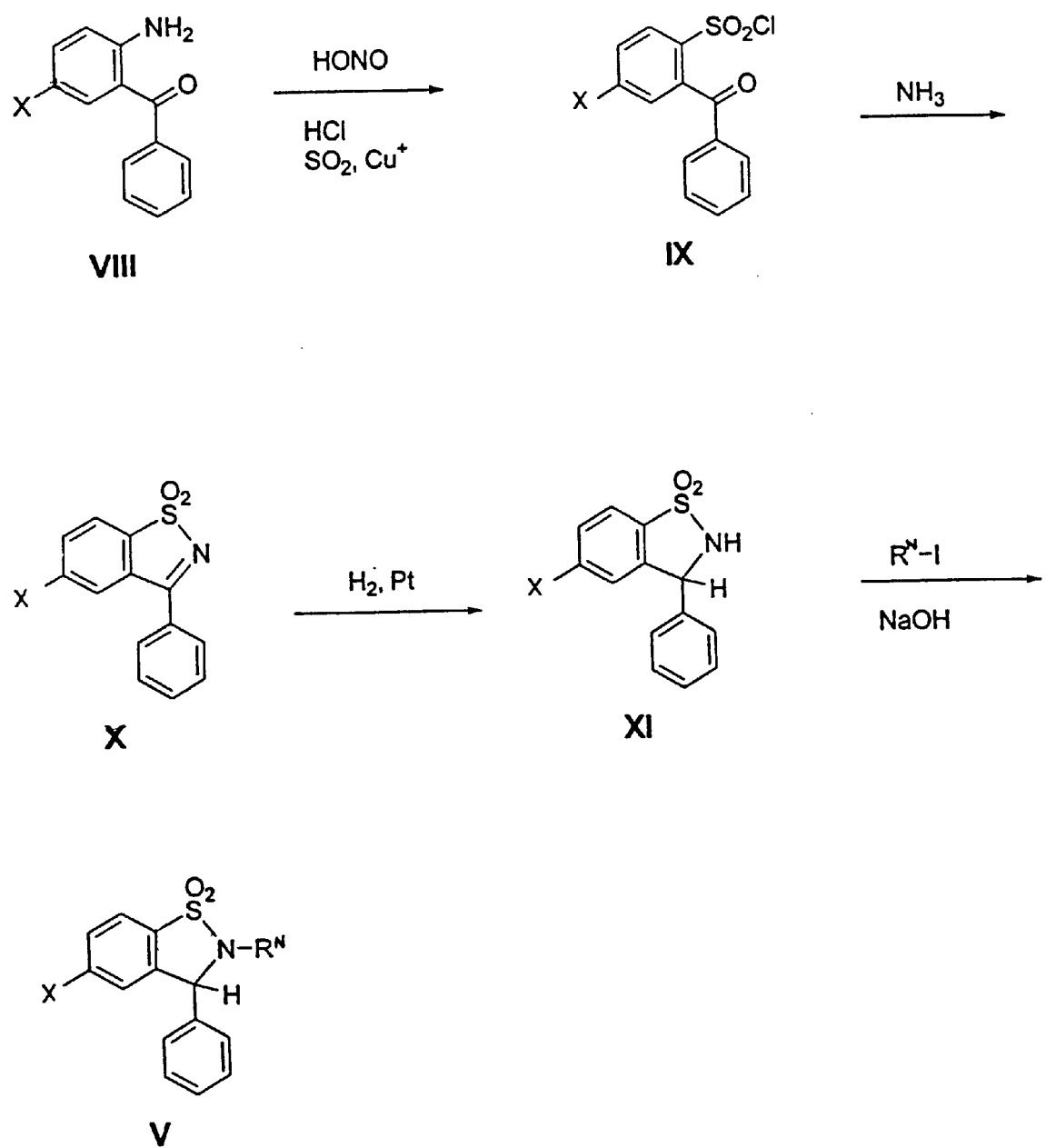
FIG. 4 shows the method for synthesis of sultams wherein ring A is halo-substituted.

A Method of Synthesizing Sultams V Wherein $R^A$ is a Halogen, such as Chlorine, Bromine or Iodine The method is illustrated in FIG. 4. For sultams with halo-substitution on ring A in the 5-position, the method using alkyllithium reagent is not suitable due to the possibility of metal-halogen exchange between the lithium and the halogen substituent on ring A, which may cause dehalogenation and other side reactions. An alternative synthesis of such compounds was developed.

Sultam V, wherein $R^N$ is methyl, ethyl, or propyl, was synthesized by adapting the method of Wright, J. B. (1968) *J. Heterocycl. Chem.* 5:453–459. By using a different starting reactant VIII as shown in FIG. 4, halogen-substituted o-aminobenzophenone, the alkylation by lithium reagent to install the carbonyl functionality was found to be unnecessary. Reactant VIII undergoes diazotization using HONO followed by treatment with sulfur dioxide in the presence of cuprous ion to form o-benzoylbenzenesulfonyl halide IX. The reaction of IX in concentrated ammonium hydroxide cyclizes ring B of compound X. The imine functionality on compound X is reduced by hydrogenation in the presence of platinum catalyst to yield compound XI, which is then alkylated with the selected alkyl halide-NaOH mixture to produce the sultam V, wherein $R^A$=5-chloro, 5-bromo, or 5-iodo and $R^N$=alkyl. The hydrogenated product is 5-substituted chloro-, bromo-, or iodo-. To obtain halogen sultams substituted in ring A on a carbon other than 5-carbon atom, an appropriate amino compound such as 2-amino-4-chloro-substituted benzophenone is selected.

Ring C Substituents

The substituents on ring C are determined by the substituents on the aldehyde or the ketone reactant. Other than a phenyl ring, ring C can be 2-furyl when 2-furfural is the reactant. Likewise, the nature of the sulfonyl chloride selected, in this illustration phenyl sulfonyl chloride, determines the nature of substituent $R^A$. When a sulfonyl chloride is selected, which is an aryl sulfonyl other than phenyl, like 4-pyridyl, compound VI is obtained wherein ring C is 4-pyridinyl.

Figure 5:
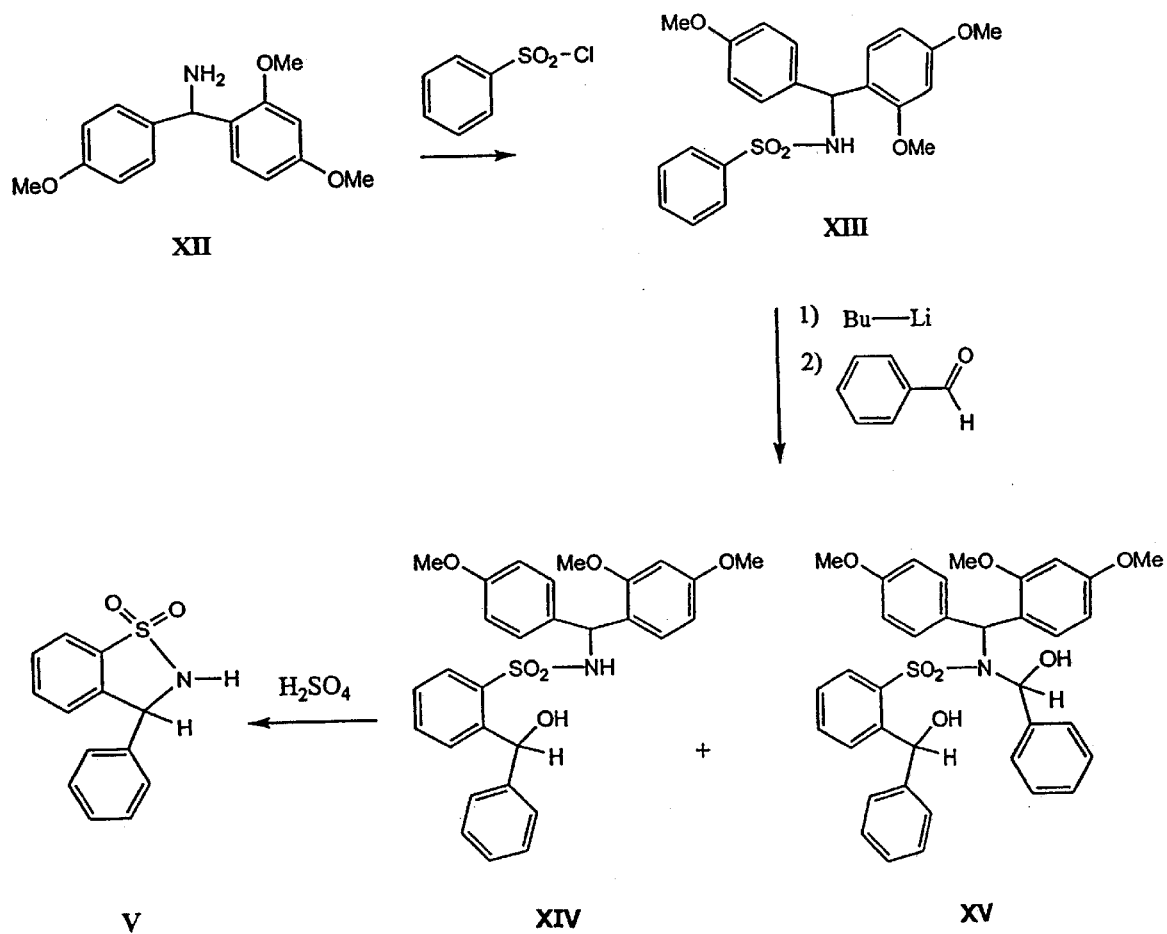
FIG. 5 shows the synthesis of sultams wherein all R groups are hydrogens.

Synthesis of Sultam V from 2,4-(dimethoxyphenyl)-(4-methoxyphenyl)methylamine In still another variant of the invention, sultams of general formula V may be synthesized from 2,4-(dimethoxyphenyl)-(4-methoxyphenyl)methylamine. An example of the reaction is shown in FIG. 5, wherein $R^A$, $R^N$, $R^Q$ and $R^C$ are all hydrogen. In that case, 2,4-(dimethoxyphenyl)-(4-methoxyphenyl)methylamine is reacted with benzenesulfonyl chloride in the presence of a base to form a sulfonamide. The preferred formula is shown by Formula XIII. Compound XIII is deprotonated and lithiated with the subsequent addition of an aromatic aldehyde or ketone to form intermediates of compounds XIV and XV. XV is the bialkylated form of the monoalkylated version in compound XIV. The intermediates XIV and XV are then reacted with a strong acid such as sulfuric acid to produce a sultam of Formula V.

Method of Synthesizing Sultam V from t-Butylamine

Figure 6:
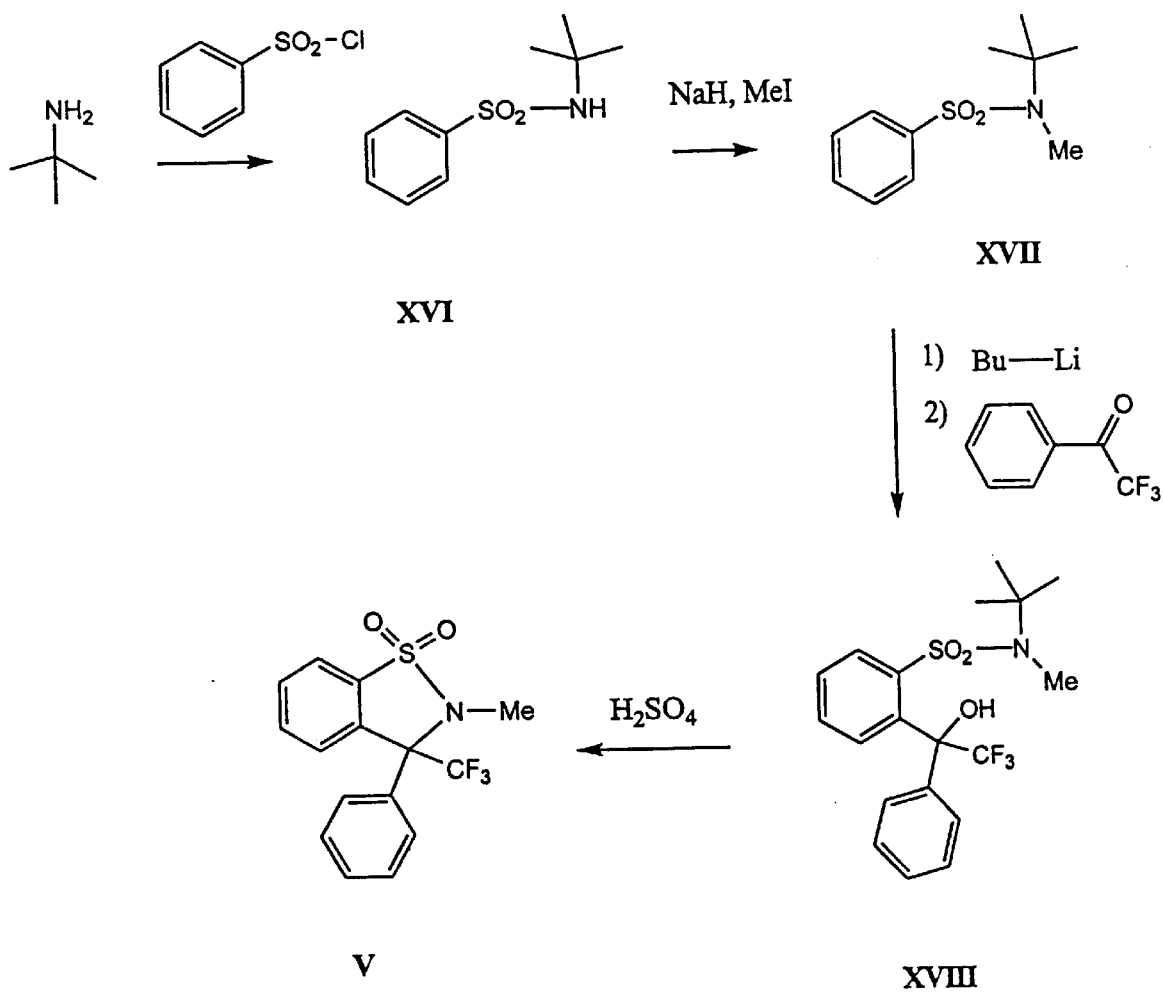
FIG. 6 shows the synthesis of sultams wherein $R^Q$ is $CF_3$.

In still another variant of the synthesis of sultam V, the starting material may be t-butylamine. A preferred general schematic of the reaction is shown in FIG. 6, wherein $R^A$ and $R^C$ are hydrogen, $R^N$ is a methyl group, and $R^Q$ is $CF_3$. t-Butylamine is reacted with benzenesulfonyl chloride to form a sulfonamide, preferably as shown by the Formula XVI in FIG. 6. The sulfonamide is reacted with sodium hydride and methyl iodide to form a compound such as that shown in FIG. 6 by XVII. The resulting compound is lithiated and alkylated to form an alkylated compound as shown in XVIII. Subsequently, compound XVIII is treated with sulfuric acid to produce the sultam of Formula V. In this way, compounds are produced with $R^Q=CF_3$, which are difficult to synthesize by other procedures.

Identification of the Absolute Configuration of the Sultams

To facilitate identification of the absolute configuration of the sultams of the invention, the chirality is determined as follows: When the optical rotation is measured in a polarimeter, the sign of rotation can be either positive or negative at a given wavelength of light. An optical rotation of 0 (zero) is also possible, in which case one must examine the rotation at another wavelength. The expression (+) and (−) indicates the physical properties of this compound, but tells nothing about the absolute stereochemistry. A pair of enantiomers have the same magnitude of optical rotation (°) but different signs. To define a chiral center with exact spacial relationship, four substituents are prioritized by the atomic number of the first atom(s) of the substituents from the chiral center. This is termed the Cahn-Ingold-Prelog system as is known in the art.

If two or more atoms are of the same number, the next atom in the substituent is compared, and so on. The group with the least priority is set behind an imaginary plane and the other three are arranged on the plane, without changing their relative positions. A circle is drawn from the most prioritized to the second, then to the third prioritized group. If the circle is clockwise, the absolute configuration is an "R" configuration; if the circle is counterclockwise, it is an "S" configuration. A pair of enantiomers (with one or more chiral centers) have an opposite sign for (R) and (S) at all chiral centers. A pair of diastereomers are isomers in which not all chiral centers are opposite. The (+)(−) signs are not by definition related to the absolute configuration (R) or (S). In this text, however, the (+) isomer was determined to be the (S) isomer, except for substituents at C-2 for the ring C phenyl group that have a priority greater than a carbon atom, in which case the priority is (R).

Separation of Enantiomers

Whenever a racemic mixture of a compound of the invention is obtained and separation into the pure enantiomers is desired, the following several procedures can be performed. The resulting racemic sultams can be separated by several chemical methods. In chiral column chromatography, for instance, using a Chiralcel OD HPLC column, one enantiomer can be eluted from the column faster than the other, thereby allowing for the separation. Otherwise, the two enantiomers can be derivatized to diastereomers by reacting them with optically active reagents whose groups can later be removed. The two diastereomers can be separated by their different physical and chemical properties, for example, by distillation (if the compounds are volatile), recrystallization (if at least one of the compounds can be crystallized), and chiral or achiral column chromatography. After the separation, the chiral auxiliaries can be cleaved and the two enantiomeric sultams obtained. Such methods are known in the art, and are taught, for example, by Eliel et al. (Ref. 19).

EXAMPLES

General Methods

Melting points were determined by capillary method and are uncorrected. Analytical TLC was performed on aluminum-backed plates coated with E. Merck Silica Gel-60 F-254. The developed plates were air-dried and irradiated with UV light and/or by spray-heat development using a p-anisaldehyde-sulfuric acid reagent. Flash column chromatography was performed on Silica Gel-60 (230–400 mesh). All HPLC separations were carried out on a Beckman System Gold instrument using Diacel's Chiralcel OD HPLC (25 cm×1 cm i.d.) column. The retention times reported were for analytical scale (20 μL) injections. Optical rotations were measured with Perkin-Elmer Model 243 automatic polarimeter for solutions in a 1-dm cell at the indicated temperature. $^1H$ and $^{13}C$ NMR spectra were recorded at 250.13 MHz and 62.89 MHz, respectively, on a Bruker AC 250 instrument or at 400.13 MHz and 100.61 MHz, respectively, on a Bruker AMX400 instrument using the indicated solvent. $^1H$ NMR shifts are reported as ppm downfield from tetramethylsilane (TMS), which was used as

Example 1

Synthesis of (R,S)-2,5-dimethyl-3-phenyl-2,3-dihydrobenzo[d]isothiazole 1,1-dioxide (V in FIG. 1, where $R^A$=5-Me, $R^C$=H, $R^N$=Me and $R^Q$=H). N-Methyl-p-toluenesulfonamide (II)

To methylamine (40%, 4.48 mL) in water (45 mL) containing NaOH pellets (2.10 g, 52.5 mmol) was added at 0° C. p-toluenesulfonyl chloride (I, $R^A$=H, 10.0 g, 52.5 mmol) over 5 min. The reaction mixture was stirred for 3 h at 0° C., then diluted with water and extracted with ethyl acetate (3 %, 30 mL). The ethyl acetate layer was washed with brine (saturated NaCl), dried over anhydrous $MgSO_4$, and concentrated to obtain a white-colored solid. The crude product was chromatographed on a silica gel column using hexanes-ethyl acetate (3:1) as the eluent to afford II (8.75 g, 90%): mp 75–77° C.; $^1H$ NMR (TMS) 7.76 (d, 2H, J=8.3 Hz), 7.32 (d, 2H, J=8.2 Hz), 4.73 (bs, 1H), 2.63 (d, 3H, J=3.9 Hz), 2.43 (s, 3H); $^{13}C$ NMR (CDCl$_3$) 143.44, 135.71, 129.67, 127.22, 29.23, 21.46.

(R,S)-2-(hydroxyphenylmethyl)-4,N-dimethylbenzenesulfonamide (IV)

Dry THF (22 mL) was added to II (1.0 g, 5.4 mmol) in a round bottom flask. Nitrogen was run into the flask, and the flask was cooled to 0° C. while stirring. N-Butyllithium (5.4 mL of a 2.5 M solution in hexanes, 13.5 mmol) was then added to the reaction over 3–4 min and left to stir at 0° C. for 30 min. To this mixture was added a solution of benzaldehyde (III in FIG. 1, 0.92 g in 9 mL dry THF, 8.6 mmol) over 4 min. This was allowed to stir for 45 min. Next, HCl (5%, 15 mL) was added, and the reaction mixture was allowed to warm to room temperature. The THF layer was separated from the aqueous layer, and the aqueous layer was extracted with ether (3% 20 mL). The combined organic layer was washed with brine, dried with anhydrous $MgSO_4$, and concentrated. The crude product was chromatographed on silica gel using hexanes-ethyl acetate (1:1) to yield IV (1.4 g, 86%) as a white solid: mp 178–179° C.; $^1H$ NMR (TMS) 7.88 (d, 1H, J=7.9 Hz), 7.36 (m, 5H), 7.25 (m, 2H), 6.57 (d, 1H, J=4.7 Hz), 3.94 (q, 1H, J=5.2 Hz), 3.48 (d, 1H, J=5.8 Hz), 2.38 (s, 3H), 2.34 (d, 3H, J=5.4 Hz); $^{13}C$ NMR (CDCl$_3$), 143.89, 141.95, 141.61, 132.94, 131.22, 130.89, 128.56, 128.37, 127.91, 126.94, 72.30, 29.27, 21.46.

(R,S)-2,5-Dimethyl-3-phenyl-2,3-dihydrobenzo[d]isothiazole 1,1-dioxide (V)

To IV (0.500 g, 1.72 mmol) in a 50 mL round bottom flask was added concentrated $H_2SO_4$ (5.0 mL) at room temperature, and the reaction mixture was stirred at that temperature for 1.5 h. The mixture was then poured into ice and extracted with $CH_2Cl_2$ (3% 15 mL), washed with saturated NaCl, dried with anhydrous $MgSO_4$, and concentrated to remove the solvent. The crude product was chromatographed on silica gel using hexanes-ethyl acetate (3:1) to obtain compound V (0.39 g, 83%) as a white solid: mp 165–167° C.; $^1H$ NMR (TMS) 7.70 (d, 1H, J=8.0 Hz), 7.35 (m, 6H), 6.82 (s, 1H), 5.15 (s, 1H), 2.74 (s, 3H), 2.31 (s, 3H); $^{13}C$ NMR (CDCl$_3$) 143.81, 138.44, 136.65, 131.18, 130.10, 128.95, 128.90, 127.97, 120.61, 66.69, 27.22, 21.51. Anal. Calcd for $C_{15}H_{15}NO_2S$ 0.15$H_2O$: C 65.26, H 5.59, 5.07, S 11.62. Found: C 65.13, H 5.56, N 5.02, S 11.65.

Example 2

Removal of a Protecting Group from an Hydroxyl Sultam (VI in FIG. 2, where $R^A$=H, $R^N$=Me, $R^Q$=H, $R^C$=4-OH) (R,S)-4-(2-Methyl-1,1-dioxo-2,3-dihydrobenzo[d]isothiazol-3-yl)phenol (VI)

To V ($R^A$=H, $R^N$=Me, $R^Q$=H, $R^C$=4-OMe, 0.230 g, 0.795 mmol) in dry $CH_2Cl_2$ (15 mL) was added $BBr_3$ (99+%, 0.298 g, 1.19 mmol) at −78° C. under $N_2$, and the reaction mixture was allowed to gradually warm to room temperature. The reaction was complete in 2.5 h, and the mixture was then poured into ice and extracted with $CH_2Cl_2$ (3% 20 mL), washed with saturated NaCl, dried with anhydrous $MgSO_4$, and concentrated to remove the solvent. The crude product was chromatographed on silica gel using hexanes-ethyl acetate (1:1) to obtain compound VI (0.206 g, 94%) as a white solid: mp 183° C.; $^1H$ NMR (TMS) 7.79 (m, 1H), 7.54 (m, 2H), 7.09 (m, 3H), 6.80 (d, 2H, J=8.6 Hz), 5.21 (s, 1H), 2.66 (s, 3H); $^{13}C$ NMR (CD$_3$OD) 159.35, 140.55, 135.18, 134.33, 130.67, 130.48, 128.66, 126.45, 121.60, 116.83, 67.60, 27.25. Anal. Calcd for $C_{14}H_{13}NO_3S$: C 61.07, H 4.76, N 5.09, S 11.65. Found: C 60.92, H 4.82, N 5.01, S 11.64.

Example 3

Synthesis of Enantiomerically Pure Sultams VIa and VIb from Sultam VI (FIG. 3, where $R^A$=H, $R^N$=Me, $R^Q$=H, $R^C$=4-OH). (1S,4R)-(+)-4,7,7-Trimethyl-2-oxa-3-oxobicyclo[2.2.1]heptane-1-carboxylic acid 4-[(3S)-2-methyl-1,1-dioxo-2,3-dihydrobenzo[d]isothiazol-3-yl]phenyl ester (VIIa) and (1S,4R,)-(−)-4,7,7-trimethyl-2-oxa-3-oxobicyclo[2.2.1]heptane-1-carboxylic acid 4-[(3R)-1,1-dioxo-2-methyl-2,3-dihydrobenzo[d]isothiazol-3-yl]phenyl ester (VIIb)

To VI (FIG. 3, where $R^A$=H, $R^N$=Me, $R^Q$=H, $R^C$=4-OH, 0.197 g, 0.715 mmol) and DMAP (0.350 g, 2.86 mmol) in dry $CH_2Cl_2$ (15 mL) was added (−)-camphanic acid chloride (0.233 g, 1.07 mmol) under $N_2$ at 0° C. The reaction mixture was allowed to warm to room temperature and to stir at that temperature for 1 h. The reaction was quenched with water (30 mL) and extracted with $CH_2Cl_2$ (3%, 20 mL). The organic layer was washed with saturated NaCl, dried with anhydrous $MgSO_4$, and concentrated to remove the solvent. The crude product was chromatographed on a silica gel column using hexanes-ethyl acetate (1:1) as the eluent to obtain a mixture of two diastereomers (VIIa+VIb, 0.277 g, 85%). The two diastereomers (VIIa+VIIb, 150 g) were separated on a Chiralcel OD HPLC column (25 cm×1 cm i.d.) using hexanes-2-propanol (8:2) as the eluent and a flow rate of 3 mL/min to yield VIIa (0.054 g) as the 1st fraction: $t_R$=32.3 min; mps 251° C.; [α]20D+84° (c 1.0, CHCl$_3$); $^1H$ NMR (TMS) 7.86 (m, 1H), 7.54 (m, 2H), 7.40 (d, 2H, J=8.4 Hz), 7.20 (d, 2H, J=8.4 Hz), 7.05 (m, 1H), 5.22 (s, 1H), 2.79 (s, 3H), 2.57 (m, 1H), 2.20 (m, 1H), 2.01 (m, 1H), 1.77 (m, 1H), 1.16 (d, 6H, J=4.5 Hz), 1.11 (s, 3H); $^{13}C$ NMR (CDCl$_3$) 177.65, 165.92, 150.47, 137.85, 134.91, 133.98, 133.05, 129.49, 129.37, 124.95, 122.12, 121.15, 90.67, 66.26, 54.84, 54.68, 30.74, 28.88, 27.46, 16.83, 9.63. Anal. Calcd for $C_{24}H_{25}NO_6S$: C 63.28, H 5.53, N 3.07, S 7.04. Found: C 63.22, H 5.54, N 3.06, S 6.96.

Compound VIIb (0.051 g) was obtained as the 2nd fraction: $t_R$=43.5 min; mp 239–240° C.; [α]20D −100° (c 1.0, $CHCl_3$); $^1$H NMR (TMS) 7.86 (m, 1H), 7.54 (m, 2H), 7.40 (d, 2H, J=8.4 Hz), 7.20 (d, 2H, J=8.3 Hz), 7.05 (m, 1H), 5.22 (s, 1H), 2.78 (s, 3H), 2.57 (m, 1H), 2.20 (m, 1H), 2.01 (m, 1H), 1.77 (m, 1H), 1.17 (d, 6H, J=3.3 Hz), 1.10 (s, 3H); $^{13}$C NMR ($CDCl_3$) 177.62, 165.88, 150.43, 137.83, 134.89, 133.94, 133.04, 129.46, 129.35, 124.94, 122.08, 121.10, 90.65, 66.23, 54.81, 54.65, 30.71, 28.86, 27.43, 16.82, 9.68. Anal. Calcd for $C_{24}H_{25}NO_6S$: C 63.28, H 5.53, N 3.07, S 7.04. Found: C 63.24, H 5.53, N 2.97, S 6.99. A mixed fraction (0.040 g) of the two distereomers (VIIa+VIIb) was obtained due to partial overlap of the two.

(+)-4-[(3S)-2-Methyl-1,1-dioxo-2,3-dihydrobenzo[d]isothiazol-3-yl]phenol (VIa)

To VIIa (0.033 g, 0.071 mmol) was added 40% $NH_3$ in MeOH (1 mL) at room temperature. The reaction mixture was stirred at this temperature for 1.5 h and then concentrated to remove excess of $NH_3$ and solvent. The crude product was chromatographed on a silica gel column using hexanes-ethyl acetate (2:1) as the eluent to yield VIa (0.019 g, 95%) as a white solid: $t_R$=21.5 min on a Chiralcel OD HPLC column using hexanes-2-propanol (85:15) as the eluent, flow rate=3 mL/min; mp 178–180° C.; [α]20D +102° (c 0.8, $CH_3OH$); $^1$H NMR (TMS) 7.81 (m, 1H), 7.58 (m, 2H), 7.11 (m, 3H), 6.80 (d, 2H, J=8.6 Hz), 5.24 (s, 1H), 2.68 (s, 3H); $^{13}$C NMR ($CD_3OD$) 159.44 140.65, 135.30, 134.34, 130.69, 130.51, 128.72, 126.48, 121.64, 116.84, 67.68, 27.24. Anal. Calcd for $C_{14}H_{13}NO_3S$: C 61.07, H 4.76, N 5.09, S 11.65. Found: C 60.97, H 4.77, N 5.01, S 11.59.

(−)-4-[(3R)-2-Methyl-1,1-dioxo-2,3-dihydrobenzo-[d]-isothiazol-3-yl]phenol (VIb)

In a similar manner compound VIIb (0.036 g, 0.078 mmol) yielded the other enantiomer VIb (0.020 g, 91%) as a white solid: $t_R$=25.8 min on a Chiralcel OD HPLC column using hexanes-2-propanol (85:15) as the eluent, flow rate=3 mL/min; mp 178–179° C.; [α]20D −105° (c 0.85, $CH_3OH$); $^1$H NMR (TMS) 7.81 (m, 1H), 7.57 (m, 2H), 7.11 (m, 3H), 6.81 (d, 2H, J=8.6 Hz), 5.23 (s, 1H), 2.68 (s, 3H); $^{13}$C NMR ($CD_3OD$) 159.42, 140.64, 135.28, 134.36, 130.69, 130.51, 128.72, 126.48, 121.64, 116.84, 67.68, 27.25. Anal. Calcd for $C_{14}H_{13}NO_3S$: C 61.07, H 4.76, N 5.09, S 11.65. Found: C 60.97, H 4.71, N 5.05, S 11.56.

Example 4

Synthesis of Sultam V with a Halogen in the 5-position as Shown in FIG. 4

To a solution of 2.50 g (8.94 mmol) of 5-chloro-3-phenyl-1,2-dihydrobenzo-[d]-isothiazole 1,1-dioxide (Wright, J. B. (1968) *J. Heterocycl. Chem.* 5:453–459) (XI) in a mixture 20 mL of 3.1% aq NaOH and 30 mL of EtOH was added 4.0 mL (9.12 g, 64.3 mmol) of MeI, and the mixture was stirred for 21 h at room temperature, at the end of which time the reaction was complete as determined by TLC. The mixture was poured into 100 mL of water, the resulting precipitate was filtered, and the product was recrystallized from MeOH to give crystalline 54 (2.10 g, 80%): mp 166–169° C.; $^1$H NMR(TMS): 2.75 (s, 3H, NMe), 5.18 (s, 1H, H-3), 7.0–7.8 (m, 8H, ArH). $^{13}$C NMR ($CDCl_3$): 27.24, 66.25, 122.24, 125.10, 127.91, 129.18, 129.25, 129.74, 132.37, 135.67, 139.20, 140.14.

By the foregoing procedure, 2.50 g (8.94 mmol) of XI was alkylated with 6.40 mL (12.5 g, 80.0 mmol) of EtI, and the crude product was purified by column chromatography on silica gel using 9:1 hexanes-ethyl acetate to give compound 55 (2.42 g, 88%): mp 112–114° C. $^1$H NMR (TMS): 1.24 (t, 3H, $CH_3$—), 3.15 (q, 1H, ½ of $CH_2$—), 3.39 (q, 1H, ½ of $CH_2$—), 5.39 (s, 1H, H-3), 7.0–7.8 (m, 8H, ArH). $^{13}$C NMR ($CDCl_3$): 13.32, 36.88, 84.15, 122.19, 125.15, 127.82, 129.21, 129.77, 132.58, 136.49, 139.13, 140.10. Anal. Calcd for $C_{15}H_{14}ClNO_2S$: C, 58.53; H, 4.58. Found: C, 58.46; H, 4.64.

Also, by the foregoing procedure, 2.50 g (8.94 mmol) of X was alkylated with 8.00 mL (10.8 g, 88.1 mmol) of PrBr, and the crude product was purified by column chromatography on silica gel using 9:1 hexanes-ethyl acetate to give compound 56 (2.47 g, 86%). $^1$H NMR (TMS): 0.85, (t, 3H, CH3), 1.61 (m, 2H, $CH_2$), 3.13 (m, 2H, $NCH_2$), 5.37 (s, 1H, H-3), 7.0–7.8 (m, 8H, Ar). $^{13}$C NMR ($CDCl_3$): 11.22, 21.14, 44.03, 64.93, 122.24, 125.16, 127.84, 129.16, 129.77, 132.51, 136.59, 139.14, 140.11. Anal. Calcd for $C_{16}H_{16}ClNO_2S$: C, 59.71; H, 5.01. Found: C, 59.53; H, 4.95.

Other examples are set forth below in Table II wherein $R^A$, $R^N$, $R^Q$ and $R^C$ are shown on sultam VI, with the reactants listed under each substituent.

TABLE II

Illustrative Sultams of the Invention
Substituents $R^Q$ and $R^C$ originate from the same reactant, either an aldehyde or a ketone

| Compound | $R^A$ | $R^N$ | $R^Q$ | $R^C$ |
|---|---|---|---|---|
| 1 | H benzenesulfonyl halide | Me methylamine | H benzaldehyde | H |
| 2 | (S)-enantiomer of 1. | | | |
| 3 | (R)-enantiomer of 1. | | | |
| 4 | H benzenesulfonyl halide | Me methylamine | H | 3-Me m-methylbenzaldehyde |
| 5 | (S)-enantiomer of 4. | | | |
| 6 | H benzenesulfonyl halide | Me methylamine | H | 3-F m-fluorobenzaldehyde |
| 7 | (S)-enantiomer of 6. | | | |
| 8 | H benzenesulfonyl halide | Me methylamine | H | 3-Cl m-chlorobenzaldehyde |
| 9 | (S)-enantiomer of 8. | | | |
| 10 | (R)-enantiomer of 8. | | | |
| 11 | H benzenesulfonyl halide | Me methylamine | H | 3-Br m-bromobenzaldehyde |
| 12 | (S)-enantiomer of 11. | | | |
| 12a | H benzenesulfonyl halide | Me methylamine | H | 2-I o-iodobenzaldehyde |
| 13 | H benzenesulfonyl halide | Me methylamine | H | 3-I m-iodobenzaldehyde |
| 14 | H benzenesulfonyl halide | Me methylamine | H | 3-$CF_3$ m-(trifluoromethyl)-benzaldehyde |
| 15 | H benzenesulfonyl halide | Me methylamine | H | 3-OH m-hydroxy-benzaldehyde |
| 16 | H benzenesulfonyl halide | Me methylamine | H | 2-Cl o-chlorobenzaldehyde |
| 17 | H benzenesulfonyl halide | Me methylamine | H | 2-Me o-methylbenzaldehyde |
| 18 | H benzenesulfonyl halide | Me methylamine | H | 4-Me p-methylbenzaldehyde |
| 19 | (R)-enantiomer of 18. | | | |
| 20 | H benzenesulfonyl halide | Me methylamine | H | 4-OMe m-hydroxy-benzaldehyde |

TABLE II-continued

Illustrative Sultams of the Invention
Substituents $R^Q$ and $R^C$ originate from the same reactant, either an aldehyde or a ketone

| Compound | $R^A$ | $R^N$ | $R^Q$ | $R^C$ |
|---|---|---|---|---|
| 21 | (S)-enantiomer of 20. | | | |
| 21a | H benzenesulfonyl halide | Me methylamine | H | 2-Br m-iodobenzaldehyde |
| 22 | (R)-enantiomer of 20. | | | |
| 22a | H benzenesulfonyl halide | Me methylamine | H | 2-F o-fluorobenzaldehyde |
| 23 | H benzenesulfonyl halide | Me methylamine | H | 4-OMe p-methoxy-benzaldehyde |
| 24 | (R)-enantiomer of 23. | | | |
| 25 | H benzenesulfonyl halide | Me methylamine | H | NHCOCH$_3$ p-anisaldehyde |
| 26 | H benzenesulfonyl halide | Me methylamine | H | NHCOCH$_3$ 4-acetamido-benzaldehyde |
| 27 | H benzenesulfonyl halide | Me methylamine | H | 4-F p-fluorobenzaldehyde |
| 28 | H benzenesulfonyl halide | Me methylamine | H | 4-Cl p-chlorobenzaldehyde |
| 29 | H benzenesulfonyl halide | Me methylamine | H | 4-Br p-bromobenzaldehyde |
| 30 | H benzenesulfonyl halide | Me methylamine | H | 4-Ph 4-phenylbenzaldehyde |
| 31 | H benzenesulfonyl halide | Me methylamine | H | 2-Me, 5-Me 2,5-dimethyl-benzaldehyde |
| 32 | H benzenesulfonyl halide | Me methylamine | H | 2-Cl, 3-Cl 2,3-dichloro-benzaldehyde |
| 33 | H benzenesulfonyl halide | Me methylamine | H | 2-Cl, 6-Cl 2,6-dichloro-benzaldehyde |
| 34 | H benzenesulfonyl halide | Me methylamine | H | F$_5$ pentafluorobenzaldehyde |
| 35 | H benzenesulfonyl halide | H ammonia | H | H benzaldehyde |
| 36 | H benzenesulfonyl halide | H ammonia | H | 3-Cl m-chloro-benzaldehyde |
| 37 | H benzenesulfonyl halide | Et ethylamine | H | 3-Cl m-chloro-benzaldehyde |
| 38 | H benzenesulfonyl halide | Bu N-butylamine | H | 3-Cl m-chloro-benzaldehyde |
| 39 | H benzenesulfonyl halide | t-Bu t-butylamine | H | 3-Cl m-chlorobenzaldehyde |
| 40 | H benzenesulfonyl halide | Ph aniline | H | H benzaldehyde |
| 41 | H benzenesulfonyl halide | Isopropyl isopropyl-amine | H | H benzaldehyde |
| 42 | H benzenesulfonyl halide | Me methylamine | Me | H acetophenone |
| 43 | H benzenesulfonyl halide | Me methylamine | Me | 2-Cl o-chlorophenyl methyl ketone |
| 44 | H benzenesulfonyl halide | Me methylamine | Me | 3-Cl m-chlorophenyl methyl ketone |
| 45 | H benzenesulfonyl halide | Me methylamine | Me | 3-OH m-hydroxyphenyl methyl ketone |
| 46 | H benzenesulfonyl halide | Me methylamine | CF$_3$ trifluoromethyl phenyl ketone | H |
| 47 | 5-Me p-toluenesulfonyl halide | Me methylamine | H | H benzaldehyde |
| 48 | 5-Me p-toluenesulfonyl halide | Me methylamine | H | 3-Cl m-chlorobenzaldehyde |
| 49 | 5-Me p-toluenesulfonyl halide | Me methylamine | H | 4-F p-fluorobenzaldehyde |
| 50 | 5-Me p-toluenesulfonyl halide | Me methylamine | H | H(a) 2-furfural |
| 51 | H benzenesulfonyl halide | Me methylamine | Me | 4-OH p-hydroxyphenyl methyl ketone |
| 52 | 5-Me p-toluenesulfonyl halide | Me methylamine | H | 4-OMe p-methoxybenzaldehyde |
| 53 | 5-Me p-toluenesulfonyl halide | Me methylamine | Me | H acetophenone |
| 54 | 5-Cl 2-amino-5-chlorobenzoyl-benzophenone | Me methyl iodide | H | H |
| 55 | 5-Cl 2-amino-5-chlorobenzoyl-benzophenone | Et ethyl iodide | H | H |
| 56 | 5-Cl 2-amino-5-chlorobenzoyl-benzophenone | Propyl propyl iodide | H | H |

(a)The ring is furyl.

BIOLOGICAL ACTIVITIES OF THE COMPOUNDS OF THE INVENTION

Introduction

In studies in conjunction with the invention, it was found that the anti-HIV activity of the compounds of the invention varied in an unforeseeable manner depending on the nature of the individual substituents, on the size and bulkiness of the substituents, on their polarity, the ring on which and at which position the substituent(s) is linked, whether or not the nitrogen is substituted, and by what substituent, whether there was a substituent on the stereogenic center at C-3, and in what position (ortho-, meta-, or para-) the substituents were linked on the C ring of the sultams. From the data of anti-HIV structure-activity relationships, it was thus observed that both steric and electronic factors played an important role. These studies further suggested that the most active sites for substitutions to be positioned is on the nitrogen of the B ring and the ortho- or meta-position of the C ring.

Antiviral/anti-HIV Activity of the Sultams

A primary objective of the invention was to find compounds that exhibit high activity as antiviral, especially anti-HIV activity. Indeed, as described, the sultams of the invention are highly effective in that respect, whether as racemates, or when resolved in their respective (+)-enantiomers. The sultams of the invention have biological activity that make them interesting candidates for biological applications other than (or in addition to) anti-HIV drugs. It is not excluded that they may have fungicidal or insecticidal properties or the ability to control other undesirable microorganisms, which is of interest in agricultural applications. Veterinary applications to control animal infections are also contemplated. The sultams of the invention are especially useful to inhibit the growth or replication of a virus in animals, especially mammals. Examples of mammals include humans, primates, bovines, ovines, porcines, felines, canines, elephantidae, etc. Examples of viruses include but are not limited to HIV-1, HIV-2, herpes simplex virus (types 1 and 2), varicella zoster virus, cytomegalovirus, papilloma virus, HTLV-1, HTLV-2, feline leukemia virus, avian sarcoma viruses such as rous sarcoma virus, hepatitis types A–E, influenza virus, measles, mumps and rubella viruses. In a presently preferred use, the compounds of the invention are used to treat a human at risk, exposed or infected (i.e., in need of such treatment) with the human immunodeficiency virus, either prophylactically or therapeutically.

The sultams of the invention are accordingly particularly useful in the treatment of infection by the human immunodeficiency virus and also in the treatment of consequent pathological conditions associated with AIDS. Treating AIDS is defined as including, but not limited to, treating a wide range of states of HIV infection: AIDS, ARC (AIDS related complex), both symptomatic and asymptomatic, and actual or potential exposure to HIV. For example, the sultams of the invention are useful in treating infection by HIV after suspected exposure to HIV by, for example, blood transfusion, exposure to patient blood during surgery, or an accidental hypodermic needle stick.

An advantage to the compounds of the invention is that they retain the ability to inhibit HIV RT mutants that are resistant to TiBO and other compounds known to inhibit RT. This is advantageous over the current AIDS drug therapy, where biological resistance tends to develop to nucleoside or non-nucleoside analogues used in the inhibition of RT.

The sultams of the invention may be assayed for antiviral activity in accordance with published protocols. They include, but are not limited to, cell count, cytopathic effect, dish-colony formation, microtiter-growth inhibition and thymidine incorporation.

In addition, the compounds of the present invention can be assayed for their ability to inhibit HIV infection via an infectivity assay. The infectivity assay comprises infection of T-lymphocytes or macrocytes/macrophages with either HIV-1 or HIV-2. At six or more days post-infection, measurement of particle-associated reverse transcriptase activity and/or p24 antigen levels can be determined (see, for example, Clapham et al. (1990) *Nature*, 337:368–370 or McDougal et al. (1985) *J. Immun. Meth.* 76:171–183. In addition, the focal infectivity assay (FIA) can be used to assay the susceptibility of HIV to antiviral agents (see, e.g., Pincus et al. (1991) *Bio. Techniques* 10:336–342. Furthermore, the levels of antiviral "activity" of the compounds of the present invention can be rapidly determined in a series of interrelated assays via a semiautomated multiparameter approach as disclosed by Gulakowski et al. (1991) *J. Virol. Meth.* 33:87–100, which is incorporated herein by reference.

The sultams of the invention were tested in accordance with the National Cancer Institute Protocol, Weislow, O. W., et al. (1989) *J. Natl. Cancer Inst.* 81:577–586, which is incorporated herein by reference. The protocol is also described in U.S. Pat. No. 5,843,990.

The anti-HIV activity of compounds of the invention illustrated by the formula VI shown above, is reported below.

Table III illustrates anti-HIV-1 activities of compounds of the invention, the substituents (shown in formula V), $R^N$, $R^Q$ and $R^A$ are represented by $R^1$, $R^2$, and $R^4$, respectively, and the benzene (and in one instance the furyl) ring C is represented by $R^3$.

TABLE III

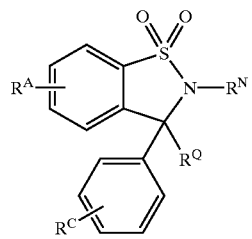

| No. | $R^N$ | $R^Q$ | Ring C | $R^A$ | Config. | Opt. Rot. (deg.) | mp (deg. C.) | $EC_{50}$ (μM) | $IC_{50}$ (μM) | $TI_{50}$ | Act.[1] |
|---|---|---|---|---|---|---|---|---|---|---|---|
| 1 | Me | H | phenyl | H | (+/−) | — | — | — | — | — | A |
| 2 | Me | H | phenyl | H | (+)-(S) | 147 | 156–157 | 0.471 | >316 | >674 | A |

TABLE III-continued

| No. | R^N | R^Q | Ring C | R^A | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 3 | Me | H | phenyl | H | (−)-(R) | −148 | 156–157 | — | >316 | — | I |
| 4 | Me | H | 3-Me-phenyl | H | (+/−) | — | 103 | 0.036 | >200 | >556 | A |
| 5 | Me | H | 3-Me-phenyl | H | (+)-(S) | 149 | 154 | 0.037 | >2.0 | >54 | A |
| 6 | Me | H | 3-F-phenyl | H | (+/−) | — | 127 | 0.173 | 66.7 | 385 | A |
| 7 | Me | H | 3-F-phenyl | H | (+)-(S) | | | — | — | — | — |
| 8 | Me | H | 3-Cl-phenyl | H | (+/−) | — | 133 | 0.36 | 113 | 297 | A |
| 9 | Me | H | 3-Cl-phenyl | H | (+)-(S) | 166 | 164 | 0.086 | >2 | >31 | A |
| 10 | Me | H | 3-Cl-phenyl | H | (−)-(R) | −150 | 160 | 5.28 | 26.8 | 5.06 | M |

TABLE III-continued
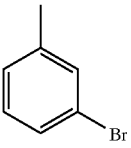
| No. | $R^N$ | $R^Q$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 11 | Me | H | 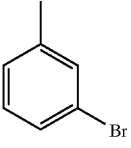 | H | (+/−) | — | 128–129 | 0.781 | 45.6 | 58.4 | A |
| 12 | Me | H | 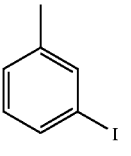 | H | (+)-(S) | 140 | 157 | 0.074 | 101 | 136.5 | A |
| 13 | Me | H | 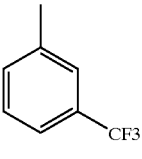 | H | (+)-(S) | 126 | 156 | 0.076 | 62.4 | 817 | A |
| 14 | Me | H | 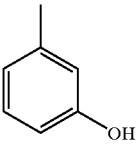 | H | (+/−) | — | 97–98 | 0.653 | 48 | 73.5 | A |
| 15 | Me | H | 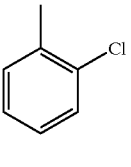 | H | (+/−) | — | 155–156 | 38.7 | >30 | >1.3 | M |
| 16 | Me | H | 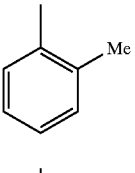 | H | (+/−) | — | 156 | 0.093 | >11 | >119 | A |
| 17 | Me | H | 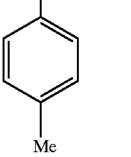 | H | (+)-(S) | 155 | 152 | 4.68 | 123 | 26.3 | M |
| 18 | Me | H |  | H | (+)-(S) | 131 | 128–129 | 1.53 | 138 | 90.4 | A |

TABLE III-continued
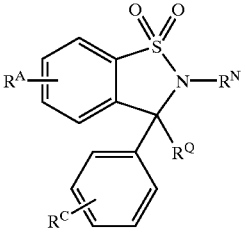
| No. | $R^N$ | $R^Q$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 19 | Me | H | 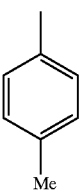 | H | (−)-(R) | −127 | 126–127 | — | — | — | I |
| 20 | Me | H | 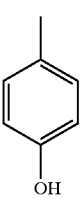 | H | (+/−) | — | 183 | — | >200 | — | I |
| 21 | Me | H | 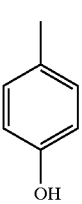 | H | (+)-(S) | 102 | 178–180 | — | >200 | — | I |
| 22 | Me | H | 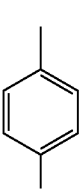 | H | (−)-(R) | −105 | 178–179 | — | >200 | — | I |
| 23 | Me | H | 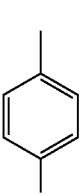 | H | (+)-(S) | 119 | 166–167 | — | >200 | — | I |
| 24 | Me | H | 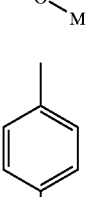 | H | (−)-(R) | −120 | 166 | — | >200 | — | I |

TABLE III-continued
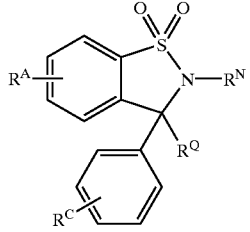
| No. | R$^N$ | R$^Q$ | Ring C | R$^A$ | Config. | Opt. Rot. (deg.) | mp (deg. C.) | EC$_{50}$ ($\mu$M) | IC$_{50}$ ($\mu$M) | TI$_{50}$ | Act.[1] |
|---|---|---|---|---|---|---|---|---|---|---|---|
| 25 | Me | H | 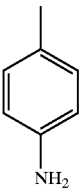 | H | (+/−) | — | 219–220 | 65 | >200 | >3.08 | I |
| 26 | Me | H |  | H | (+/−) | — | 221 | — | >200 | — | I |
| 27 | Me | H | 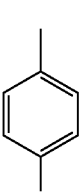 | H | (+/−) | — | 111–112 | 37.5 | 161 | 4.29 | M |
| 28 | Me | H | 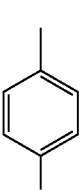 | H | (+/−) | — | 132–133 | 19.6 | 29 | 1.48 | I |
| 29 | Me | H | 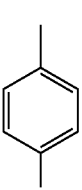 | H | (+/−) | — | 135 | 11.02 | 36.8 | 3.34 | M |
| 30 | Me | H | 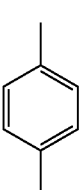 | H | (+/−) | — | 188 | — | >200 | — | I |

TABLE III-continued
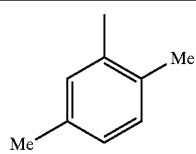
| No. | $R^N$ | $R^Q$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 31 | Me | H | 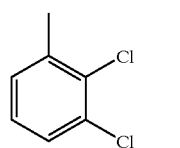 | H | (+/−) | — | 168–169 | 0.512 | >200 | >390 | A |
| 32 | Me | H | 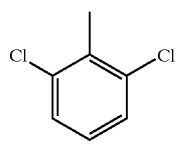 | H | (+/−) | — | 160–161 | 0.039 | >200 | >51.2 | A |
| 33 | Me | H | 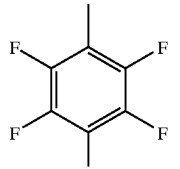 | H | (+/−) | — | 181–183 | 5.09 | 10.9 | 2.13 | M |
| 34 | Me | H | 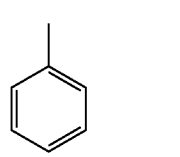 | H | (+/−) | — | 154 | 40.2 | >198 | >4.93 | M |
| 35 | H | H | 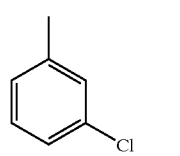 | H | (+/−) | — | — | — | — | — | — |
| 36 | H | H | 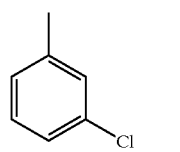 | H | (+/−) | — | 142–143 | 33.8 | 427 | 12.6 | M |
| 37 | Et | H | 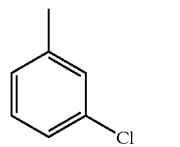 | H | (+/−) | — | 100–101 | 0.167 | 39.7 | 238 | A |
| 38 | Bu | H | 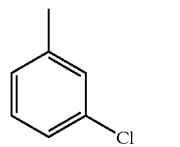 | H | (+/−) | — | 116–117 | 1.35 | 18.2 | 13.5 | M |

TABLE III-continued

| No. | $R^N$ | $R^Q$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 39 | t-Bu | H | phenyl | H | (+/−) | — | 162 | — | >200 | — | I |
| 40 | Ph | H | phenyl | H | (+/−) | — | 168–169 | — | >200 | — | I |
| 41 | 2-Pr | H | phenyl | H | (+/−) | — | 141 | 3.23 | 244 | 75.4 | A |
| 42 | Me | Me | phenyl | H | (+/−) | — | 170 | 4.52 | 117 | 25.9 | A |
| 43 | Me | Me | 2-Cl-phenyl | H | (+/−) | — | — | — | — | — | — |
| 44 | Me | Me | 3-Cl-phenyl | H | (+/−) | — | 118–120 | 0.198 | 32.4 | 164 | A |
| 45 | Me | Me | 3-OH-phenyl | H | (+/−) | — | 191–192 | 30.7 | >200 | >6.5 | M |
| 46 | Me | $CF_3$ | phenyl | H | (+/−) | — | 138–139 | 0.46 | 31.8 | 69.1 | A |

TABLE III-continued

[Structure: benzisothiazole 1,1-dioxide with R^A on benzene ring, R^N on nitrogen, and C3 substituted with R^Q and a phenyl ring bearing R^C]

| No. | R^N | R^Q | Ring C | R^A | Config. | Opt. Rot. (deg.) | mp (deg. C.) | EC$_{50}$ ($\mu$M) | IC$_{50}$ ($\mu$M) | TI$_{50}$ | Act.[1] |
|---|---|---|---|---|---|---|---|---|---|---|---|
| 47 | Me | H | phenyl | 5-Me | (+/−) | — | 165–167 | 31 | 156 | 5.03 | M |
| 48 | Me | H | 3-Cl-phenyl | 5-Me | (+/−) | — | — | — | — | — | — |
| 49 | Me | H | 4-F-phenyl | 5-Me | (+/−) | — | 94–95 | — | 76.9 | — | I |
| 50 | Me | H | 2-furyl | 5-Me | (+/−) | — | 151–152 | — | >200 | — | I |
| 51 | Me | H | 4-OH-phenyl | 5-Me | (+/−) | — | 210–211 | — | >140 | — | I |
| 52 | Me | H | 4-OMe-phenyl | 5-Me | (+/−) | — | 165–166 | — | >200 | — | I |
| 53 | Me | Me | phenyl | 5-Me | (+/−) | — | 148–149 | — | 107 | — | I |

TABLE III-continued

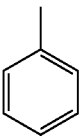

| No. | $R^N$ | $R^Q$ | Ring C | $R^A$ | Config. | Opt. Rot. (deg.) | mp (deg. C.) | $EC_{50}$ ($\mu$M) | $IC_{50}$ ($\mu$M) | $TI_{50}$ | Act.[1] |
|---|---|---|---|---|---|---|---|---|---|---|---|
| 54 | Me | H | 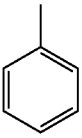 | 5-Cl | (+/−) | — | 166–169 | 26.1 | >147 | 5.63 | M |
| 55 | Et | H | 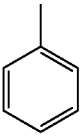 | 5-Cl | (+/−) | — | 112–114 | 19.3 | 60.6 | 3.14 | M |
| 56 | Pr | H | 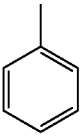 | 5-Cl | (+/−) | — | — | — | 365 | — | I |

Activities are defined as per the NCI protocol: A = "active"; M = "moderately active"; I = "inactive".
Enantiomers were separated using a ChiralCel OD HPLC column. See Experimental for details.

The most potent compounds of the invention to alleviate HIV infections are the following compounds, the numerical reference being made to Table III.

Compound 4 wherein $R^A$ is hydrogen, $R^N$ is methyl, $R^Q$ is hydrogen and Ring C is 3-methylphenyl.

Compound 5 wherein $R^A$ is hydrogen, $R^N$ is methyl, $R^Q$ is hydrogen and Ring C is 3-methylphenyl and the enantiomer is (+)-(S).

Compound 6 wherein $R^A$ is hydrogen, $R^N$ is methyl, $R^Q$ is hydrogen and Ring C is 3-fluorophenyl.

Compound 8 wherein $R^A$ is hydrogen, $R^N$ is methyl, $R^Q$ is hydrogen and Ring C is 3-chlorophenyl.

Compound 9 wherein $R^A$ is hydrogen, $R^N$ is methyl, $R^Q$ is hydrogen and Ring C is 3-chlorophenyl and the enantiomer is (+)-(S).

Compound 11 wherein $R^A$ is hydrogen, $R^N$ is methyl, $R^Q$ is hydrogen and Ring C is 3-bromophenyl.

Compound 12 wherein $R^A$ is hydrogen, $R^N$ is methyl, $R^Q$ is hydrogen and Ring C is 3-bromophenyl and the enantiomer is (+)-(S).

Compound 13 wherein $R^A$ is hydrogen, $R^N$ is methyl, $R^Q$ is hydrogen and Ring C is 3-iodophenyl and the enantiomer is (+)-(S).

Compound 16 wherein $R^A$ is hydrogen, $R^N$ is methyl, $R^Q$ is hydrogen and Ring C is 2-chlorophenyl.

Compound 32 wherein $R^A$ is hydrogen, $R^N$ is methyl, $R^Q$ is hydrogen and Ring C is 2,3-dichlorophenyl.

Compound 44 wherein $R^A$ is hydrogen, $R^N$ is methyl, $R^Q$ is methyl and Ring C is 3-chlorophenyl.

Compound 37 wherein $R^A$ is hydrogen, $R^N$ is ethyl, $R^Q$ is hydrogen and Ring C is 3-chlorophenyl.

All compounds shown above are racemic mixtures except where otherwise specified. In all examples evaluated, the (+)-S enantiomers except for examples in which (e.g., 3-(2-chlorophenyl)) Cahn-Ingold-Prelog priorities are reversed and the chirality becomes (R) are the most active compounds of a pair of enantiomers.

It is to be noted that the term "inactive" refers only to the response is the Weislow protocol. These compounds are active in screening tests for inhibition of reverse transcriptase.

As is apparent from the teaching of the disclosure, a principal objective of the invention was to find compounds that exhibit very high activity in the Weislow protocol. However, compounds other than those that excel in that activity are expected to have biological activity that make them interesting candidates for biological applications other than as anti-HIV drugs.

Pharmaceutical Compositions

Pharmaceutical compositions that comprise one or more compounds of the invention may be formulated, as is well known in the prior art, such as by reference to known compilations as Remington's Pharmaceutical Sciences, Mack Publishing Co., Easton, Pa., USA. The dosage ranges for administration of the compounds of the invention are those needed to produce the desired affect without undue toxicity, whereby symptoms of infection are ameliorated.

The pharmaceutical composition may contain other pharmabiologically active compounds in a mixture with the compounds of the invention, to treat (therapeutically or prophylactically) acquired immunodeficiency syndrome (AIDS). For example, other active compounds may include, but are not limited to, other antiviral compounds (e.g., AZT, ddC, TiBO derivatives, acyclovir, alpha-interferon), immunostimulants (e.g., various interleukins and cytokines), immunomodulators and antibiotics (e.g., antibacterial, antifungal, anti-pneumocystis agents), even when these do not show potent activity in the NCI Weislow protocol.

In addition, the compounds of the invention, like HIV reverse transcriptases, are useful as tools and/or reagents to study inhibition of retroviral reverse transcriptases. Hence, the compounds are useful as a SAR (structure-activity relationships) tools to study, select and/or design other molecules to inhibit HIV.

The active compounds described in this text are potentially useful in combination therapy with one or more of the compounds to provide an attractive regimen to halt proliferation of HIV under clinical conditions. Such agents include, but are not restricted to, inhibitors of HIV reverse transcriptase, e.g., AZT (zidovudine, Retrovir.RTM.), ddI (dideoxyinosine, didanosine, Videx.RTM.), d4T (dideoxydidehydrothymidine, stavudine), ddC (dideoxycytidine, zalcitabine), and nevirapine, among others. Combination regimens with HIV protease inhibitors might include, but are not restricted to, e.g., ritonavir (Norvir.RTM.) or saquinavir mesylate (Invirase.RTM.), among other drugs.

The preferred route of administration is oral, although other routes of administration are acceptable. The compounds may be mixed with inert materials for pharmaceutical efficacy as is known in the art. The compounds may be formulated in aqueous solution for intravenous (i.v.), intraperitoneal (i.p.), or subcutaneous (s.c.) administration. Topical applications include mixtures of the compounds with oils or fatty acid esters or as components of skin patches that are capable of delivering the drugs across the dermal layer. Aqueous solutions, or solutions in suitable carriers, may be administered intranasally.

The compounds of the invention readily lend themselves to being made part of what are called "inclusion compounds", such as with cyclodextrins and other suitable substances.

All publications referenced herein are hereby incorporated by reference in their entirety. The invention is not limited to the embodiments described herein, but encompasses all modifications within the scope of the following claims and equivalent thereof.

Typical compounds of the invention with their respective substituents are shown in Table I. Other compounds of the invention can be synthesized using other reactants that will yield the corresponding substituents on the target sultams.

We claim:

1. A sultam of the general formula VI

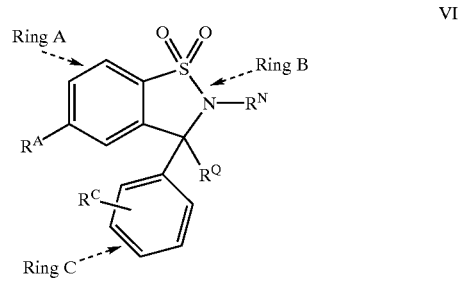

VI wherein $R^A$, $R^N$, $R^Q$, $R^C$ have the respective meaning shown

| Compound | $R^A$ | $R^N$ | $R^Q$ | $R^C$ |
|---|---|---|---|---|
| 14 | H | Me | H | 3-CF$_3$ |
| 26 | H | Me | H | NHCOCH$_3$ |
| 30 | H | Me | H | 4-Ph |
| 31 | H | Me | H | 2-Me, 5-Me |
| 32 | H | Me | H | 2-Cl, 3-Cl |
| 33 | H | Me | H | 2-Cl, 6-Cl |
| 34 | H | Me | H | F$_3$ |
| 41 | H | 2-Pr | H | H |
| 42 | H | Me | Me | H |
| 43 | H | Me | Me | 2-Cl |
| 44 | H | Me | Me | 3-Cl |
| 46 | H | Me | CF$_3$ | H |
| 47 | 5-Me | Me | H | H |
| 48 | 5-Me | Me | H | 3-Cl |
| 49 | 5-Me | Me | H | 4-F |
| 52 | 5-Me | Me | H | 4-OMe |
| 53 | 5-Me | Me | Me | H |
| 55 | 5-Cl | Et | H | H |
| 56 | 5-Cl | Propyl | H | H. |

2. A composition which comprises a biologically acceptable carrier and in a non-toxic effective amount, a compound of the following formula or a salt thereof:

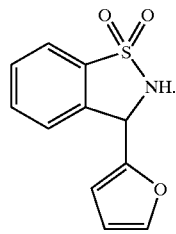

3. A method for treating a viral infection in a mammal which comprises administering to the mammal an antiviral non-toxic amount of a composition comprising a biologically acceptable carrier and in a non-toxic effective amount, a compound of the formula V or a salt thereof:

V

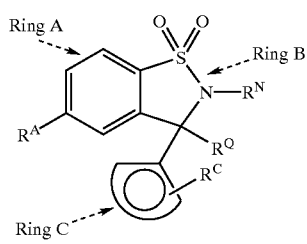

wherein $R^A$, $R^N$, $R^Q$, and $R^C$ are hydrogen.

4. A method for treating a viral infection in a mammal which comprises administering to the mammal an antiviral non-toxic amount of a composition comprising a biologically acceptable carrier and in a non-toxic effective amount, a compound of the formula VI or a salt thereof:

VI

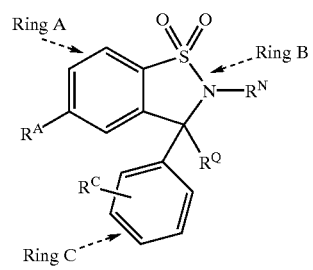

wherein $R^A$ is hydrogen, $R^N$ is methyl, $R^Q$ is hydrogen, and $R^C$ is chloro.

5. The method of claim 3 wherein the mammal is human.

6. The method of claim 4 wherein the mammal is human.

7. A composition which comprises a biologically acceptable carrier and a non-toxic effective amount of the composition of claim 1.

8. A method for treating a viral infection in a mammal which comprises administering to a mammal an antiviral nontoxic amount of the composition of claim 7.

* * * * *

UNITED STATES PATENT AND TRADEMARK OFFICE
CERTIFICATE OF CORRECTION

PATENT NO. : 6,562,850 B1
DATED : May 13, 2003
INVENTOR(S) : Baker et al.

It is certified that error appears in the above-identified patent and that said Letters Patent is hereby corrected as shown below:

Column 13,
Line 4, please change "$^{-13}C$" to -- $^{13}C$ --.

Column 22,
No. 10, at the subheading "TI $_{50}$", please change "5.06" to -- 5.08 --.

Signed and Sealed this

Second Day of December, 2003

JAMES E. ROGAN
*Director of the United States Patent and Trademark Office*